United States Patent
Sirhan et al.

(10) Patent No.: US 6,648,911 B1
(45) Date of Patent: Nov. 18, 2003

(54) METHOD AND DEVICE FOR THE TREATMENT OF VULNERABLE TISSUE SITE

(75) Inventors: Motasim Sirhan, Sunnyvale, CA (US); John Yan, Los Gatos, CA (US); Kevin Gertner, Los Gatos, CA (US)

(73) Assignee: Avantec Vascular Corporation, Sunnyvale, CA (US)

( * ) Notice: Subject to any disclaimer, the term of this patent is extended or adjusted under 35 U.S.C. 154(b) by 194 days.

(21) Appl. No.: 09/717,910

(22) Filed: Nov. 20, 2000

(51) Int. Cl.$^7$ ................................................. A61F 2/06
(52) U.S. Cl. ..................................................... 623/1.15
(58) Field of Search ................................ 623/1.15, 1.1, 623/1.11–1.22; 606/151–158, 194; 628/898

(56) References Cited

U.S. PATENT DOCUMENTS

| | | |
|---|---|---|
| 2,533,004 A | 12/1950 | Ferry et al. |
| 2,642,874 A | 6/1953 | Keeling |
| 2,854,982 A | 1/1958 | Pagano |
| 3,089,815 A | 5/1963 | Lieb et al. |
| 3,221,745 A | 12/1965 | Coover et al. |
| 3,223,083 A | 12/1965 | Cobey |
| 3,438,374 A | 4/1969 | Falb et al. |
| 3,523,807 A | 8/1970 | Gerendas |
| 3,552,986 A | 1/1971 | Bassemir et al. |
| 3,620,218 A | 11/1971 | Schmitt |
| 3,640,741 A | 2/1972 | Estes |
| 3,707,146 A | 12/1972 | Cook et al. |
| 3,723,244 A | 3/1973 | Breillatt, Jr. |
| 3,726,279 A | 4/1973 | Barefoot et al. |
| 3,749,084 A | 7/1973 | Cucchiara |
| 3,868,956 A | 3/1975 | Alfidi et al. |
| 3,880,158 A | 4/1975 | Gurney |
| 3,939,049 A | 2/1976 | Ratner et al. |
| 3,987,000 A | 10/1976 | Gleichenhagen et al. |
| 4,023,559 A | 5/1977 | Gaskell |
| 4,040,420 A | 8/1977 | Speer |
| 4,079,124 A | 3/1978 | Winchell |
| 4,080,969 A | 3/1978 | Casey et al. |
| 4,118,470 A | 10/1978 | Casey et al. |

(List continued on next page.)

FOREIGN PATENT DOCUMENTS

| | | |
|---|---|---|
| EP | 0 461 791 A1 | 12/1991 |
| EP | 0 479 557 A1 | 4/1992 |

(List continued on next page.)

OTHER PUBLICATIONS

International Search Report for PCT/US01/48354, mailed Jan. 29, 2003.

Primary Examiner—Michael J. Milano
Assistant Examiner—(Jackie) Tan-Uyen T. Ho
(74) Attorney, Agent, or Firm—Duane Morris LLP

(57) ABSTRACT

The present invention is directed to method and apparatus for treating vulnerable tissue sites, such as aneurysms in the abdominal area or in the thoracic cavity, and expanded tissues on various organs and body surfaces such as the heart. The apparatus of the present invention, are containment members for at least partially containing the vulnerable tissue site, thus preventing or minimizing the further vulnerability or growth of the site. Additionally, or alternatively, the containment members can apply resistive force to the vulnerable tissue site. The force can be compressive against the exterior surface of the tissue site. The containment members of the present invention can be used alone or in combination with support members, such as stent/grafts, in treating a tissue site. In this embodiment, the support member is disposed within the inner lumen of the vulnerable tissue site with the containment member disposed on the exterior surface of the lumen.

4 Claims, 30 Drawing Sheets

U.S. PATENT DOCUMENTS

| | | |
|---|---|---|
| 4,140,126 A | 2/1979 | Choudhury |
| 4,156,067 A | 5/1979 | Gould |
| 4,179,304 A | 12/1979 | Rossomando |
| 4,200,939 A | 5/1980 | Oser |
| 4,256,094 A | 3/1981 | Kapp et al. |
| 4,265,233 A | 5/1981 | Sugitachi et al. |
| 4,272,518 A | 6/1981 | Moro et al. |
| 4,279,795 A | 7/1981 | Yamashita et al. |
| 4,286,341 A | 9/1981 | Greer et al. |
| 4,292,299 A | 9/1981 | Suzuki et al. |
| 4,298,598 A | 11/1981 | Schwarz et al. |
| 4,300,244 A | 11/1981 | Bokros |
| 4,319,363 A | 3/1982 | Ketharanathan |
| 4,321,711 A | 3/1982 | Mano |
| 4,331,783 A | 5/1982 | Stoy |
| 4,337,327 A | 6/1982 | Stoy |
| 4,359,049 A | 11/1982 | Redl et al. |
| 4,362,567 A | 12/1982 | Schwarz et al. |
| 4,370,451 A | 1/1983 | Stoy |
| 4,373,519 A | 2/1983 | Errede et al. |
| 4,377,572 A | 3/1983 | Schwarz et al. |
| 4,379,874 A | 4/1983 | Stoy |
| 4,393,041 A | 7/1983 | Brown et al. |
| 4,394,370 A | 7/1983 | Jefferies |
| 4,414,976 A | 11/1983 | Schwarz et al. |
| 4,420,589 A | 12/1983 | Stoy |
| 4,423,099 A | 12/1983 | Mueller et al. |
| 4,427,650 A | 1/1984 | Stroetmann |
| 4,427,651 A | 1/1984 | Stroetmann |
| 4,442,655 A | 4/1984 | Stroetmann |
| 4,453,939 A | 6/1984 | Zimmerman et al. |
| 4,472,840 A | 9/1984 | Jeffries |
| 4,511,478 A | 4/1985 | Nowinski et al. |
| 4,516,276 A | 5/1985 | Mittelmeier et al. |
| 4,548,736 A | 10/1985 | Muller et al. |
| 4,600,574 A | 7/1986 | Lindner |
| 4,617,293 A | 10/1986 | Wahlig et al. |
| 4,617,932 A | 10/1986 | Kornberg |
| 4,619,913 A | 10/1986 | Luck |
| 4,619,989 A | 10/1986 | Urist |
| 4,627,879 A | 12/1986 | Rose et al. |
| 4,631,055 A | 12/1986 | Redl et al. |
| 4,631,188 A | 12/1986 | Stoy et al. |
| 4,642,120 A | 2/1987 | Nevo et al. |
| 4,673,395 A | 6/1987 | Phillips |
| 4,708,861 A | 11/1987 | Popescu |
| 4,714,457 A | 12/1987 | Alterbaum |
| 4,717,717 A | 1/1988 | Finkenaur |
| 4,741,872 A | 5/1988 | De Luca et al. |
| 4,761,471 A | 8/1988 | Urist |
| 4,789,732 A | 12/1988 | Urist |
| 4,795,741 A | 1/1989 | Leshchiner et al. |
| 4,804,691 A | 2/1989 | English et al. |
| 4,816,339 A | 3/1989 | Tu et al. |
| 4,820,626 A | 4/1989 | Williams et al. |
| 4,826,945 A | 5/1989 | Cohn et al. |
| 4,837,379 A | 6/1989 | Weinberg |
| 4,856,516 A | 8/1989 | Hillstead |
| 4,861,757 A | 8/1989 | Antoniades et al. |
| 4,874,746 A | 10/1989 | Antoniades et al. |
| 4,881,939 A | 11/1989 | Newman |
| 4,909,251 A | 3/1990 | Seelich |
| 4,928,603 A | 5/1990 | Rose et al. |
| 4,938,763 A | 7/1990 | Dunn et al. |
| 4,952,403 A | 8/1990 | Vallee et al. |
| RE33,375 E | 10/1990 | Luck et al. |
| 4,969,880 A | 11/1990 | Zamierowski |
| 4,983,581 A | 1/1991 | Antoniades et al. |
| 5,019,559 A | 5/1991 | Antoniades et al. |
| 5,023,082 A | 6/1991 | Friedman et al. |
| 5,030,215 A | 7/1991 | Morse et al. |
| 5,034,375 A | 7/1991 | Antoniades et al. |
| 5,035,887 A | 7/1991 | Antoniades et al. |
| 5,057,117 A | 10/1991 | Atweh |
| 5,059,123 A | 10/1991 | Jernberg |
| 5,074,868 A | 12/1991 | Kuzmak |
| 5,108,407 A | 4/1992 | Germia et al. ............. 606/108 |
| 5,124,155 A | 6/1992 | Reich |
| 5,139,227 A | 8/1992 | Sumida et al. |
| 5,156,620 A | 10/1992 | Pigott |
| 5,171,318 A | 12/1992 | Gibson et al. |
| 5,171,579 A | 12/1992 | Ron et al. |
| 5,176,916 A | 1/1993 | Yamanaka et al. |
| 5,202,352 A | 4/1993 | Okada et al. |
| 5,207,695 A * | 5/1993 | Trout, III .................... 600/36 |
| 5,209,776 A | 5/1993 | Bass |
| 5,211,649 A | 5/1993 | Kohler et al. |
| 5,213,580 A | 5/1993 | Slepian et al. |
| 5,217,484 A | 6/1993 | Marks ....................... 606/200 |
| 5,219,328 A | 6/1993 | Morse et al. |
| 5,219,355 A | 6/1993 | Parodi et al. |
| 5,226,877 A | 7/1993 | Epstein |
| 5,290,552 A | 3/1994 | Sierra et al. |
| 5,316,023 A | 5/1994 | Palmaz et al. ............. 128/898 |
| 5,342,393 A | 8/1994 | Stack ......................... 606/213 |
| 5,350,388 A | 9/1994 | Epstein ...................... 606/154 |
| 5,368,858 A | 11/1994 | Hunziker |
| 5,395,923 A | 3/1995 | Bui-Khac et al. |
| 5,423,829 A | 6/1995 | Pham et al. ................ 606/108 |
| 5,443,454 A | 8/1995 | Tanabe et al. |
| 5,456,713 A | 10/1995 | Chuter ........................... 623/1 |
| 5,464,471 A | 11/1995 | Whalen et al. |
| 5,476,471 A * | 12/1995 | Shifrin et al. ................ 600/37 |
| 5,507,769 A | 4/1996 | Marin et al. ................ 606/198 |
| 5,522,880 A | 6/1996 | Barone et al. ................. 623/1 |
| 5,527,355 A * | 6/1996 | Ahn ......................... 623/1.36 |
| 5,552,452 A | 9/1996 | Khadem et al. |
| 5,562,685 A | 10/1996 | Mollenauer |
| 5,571,170 A | 11/1996 | Palmaz et al. ................. 623/1 |
| 5,571,171 A | 11/1996 | Barone et al. ................. 623/1 |
| 5,571,173 A | 11/1996 | Parodi ........................... 623/1 |
| 5,573,934 A | 11/1996 | Hubbell et al. |
| 5,578,071 A | 11/1996 | Parodi ........................... 623/1 |
| 5,578,072 A | 11/1996 | Barone et al. ................. 623/1 |
| 5,585,108 A | 12/1996 | Ruddy et al. |
| 5,603,720 A * | 2/1997 | Kieturakis .................. 128/898 |
| 5,626,863 A | 5/1997 | Hubbell et al. |
| 5,628,783 A * | 5/1997 | Quiachon et al. .......... 606/194 |
| 5,643,208 A | 7/1997 | Parodi ........................ 604/96 |
| 5,665,117 A | 9/1997 | Rhodes ......................... 623/1 |
| 5,683,453 A | 11/1997 | Palmaz .......................... 623/1 |
| 5,685,847 A * | 11/1997 | Barry ........................ 604/509 |
| 5,693,083 A | 12/1997 | Baker et al. ................... 623/1 |
| 5,695,517 A | 12/1997 | Marin et al. ................ 606/198 |
| 5,702,343 A | 12/1997 | Alferness .................... 600/37 |
| 5,707,378 A | 1/1998 | Ahn et al. ................... 606/139 |
| 5,716,645 A | 2/1998 | Tse et al. |
| 5,722,989 A | 3/1998 | Fitch et al. ................. 606/205 |
| 5,735,891 A * | 4/1998 | White ........................ 606/139 |
| 5,741,274 A | 4/1998 | Lenker et al. ............. 606/142 |
| 5,741,283 A | 4/1998 | Fahy .......................... 606/157 |
| 5,749,915 A | 5/1998 | Slepian |
| 5,749,968 A | 5/1998 | Melanson et al. |
| 5,755,770 A | 5/1998 | Ravenscroft .................. 623/1 |
| 5,755,777 A | 5/1998 | Chuter ........................... 623/1 |
| 5,769,887 A | 6/1998 | Brown et al. .................. 623/1 |
| 5,785,679 A | 7/1998 | Abolfathi et al. ............ 604/51 |
| 5,843,170 A | 12/1998 | Ahn ............................... 623/1 |
| 5,868,700 A | 2/1999 | Voda |
| 5,873,906 A | 2/1999 | Lau et al. ...................... 623/1 |
| 5,876,432 A | 3/1999 | Lau et al. ...................... 623/1 |

| | | | |
|---|---|---|---|
| 5,891,128 A | 4/1999 | Gia et al. .................. 606/1 |
| 5,910,129 A | 6/1999 | Fleischman |
| 5,938,669 A | 8/1999 | Klaiber et al. ............ 606/157 |
| 5,989,244 A | 11/1999 | Gregory et al. ............ 606/8 |
| 5,997,556 A | 12/1999 | Tanner ..................... 606/153 |
| 6,007,538 A | 12/1999 | Levin ....................... 606/71 |
| 6,015,431 A | 1/2000 | Thornton et al. .......... 623/1 |
| 6,042,605 A | 3/2000 | Martin et al. ............. 623/1 |
| 6,043,273 A | 3/2000 | Duhaylongsod ......... 514/478 |
| 6,051,007 A | 4/2000 | Hogendijk et al. ....... 606/151 |
| 6,053,891 A | 4/2000 | DeCampli |
| 6,060,454 A | 5/2000 | Duhaylongsod .......... 514/26 |
| 6,063,111 A | 5/2000 | Hieshima et al. .......... 623/1 |
| 6,080,175 A | 6/2000 | Hogendijk ................. 606/185 |
| 6,087,394 A | 7/2000 | Duhaylongsod .......... 514/478 |
| 6,095,997 A | 8/2000 | French et al. .............. 604/9 |
| 6,101,412 A | 8/2000 | Duhaylongsod ........... 607/2 |
| 6,110,188 A | 8/2000 | Narciso, Jr. ................ 606/153 |
| 6,113,588 A | 9/2000 | Duhaylongsod et al. ... 606/15 |
| 6,127,410 A | 10/2000 | Duhaylongsod .......... 514/478 |
| 6,141,589 A | 10/2000 | Duhaylongsod .......... 607/10 |
| 6,156,064 A * | 12/2000 | Chouinard |
| 6,171,338 B1 * | 1/2001 | Talja et al. ................ 623/1.22 |
| 6,248,116 B1 * | 6/2001 | Chevillon et al. ......... 128/898 |

FOREIGN PATENT DOCUMENTS

| | | |
|---|---|---|
| EP | 0 539 237 A1 | 4/1993 |
| EP | 0 646 365 A1 | 4/1995 |
| EP | 0 947 180 A3 | 1/2000 |
| WO | WO 93/15671 | 8/1993 |
| WO | WO 95/08289 | 3/1995 |
| WO | WO 97/40755 | 11/1997 |
| WO | WO/ 9900055 | 1/1999 |
| WO | WO/ 99/05322 | 2/1999 |
| WO | WO/ 99/07354 | 2/1999 |
| WO | WO 99/33509 | 7/1999 |
| WO | WO 99 35979 | 7/1999 |
| WO | WO/ 99/44673 | 9/1999 |
| WO | WO/ 99/45837 | 9/1999 |
| WO | WO/ 99/45852 | 9/1999 |
| WO | WO/ 00/04819 | 2/2000 |
| WO | WO 00/16700 | 3/2000 |
| WO | WO 00/25717 | 5/2000 |
| WO | WO/ 00/29056 | 5/2000 |
| WO | WO/ 00/35515 | 6/2000 |
| WO | WO 00/43062 | 7/2000 |

* cited by examiner

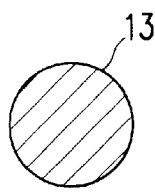
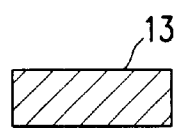
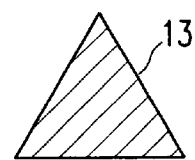
FIG. 6A          FIG. 6B          FIG. 6C
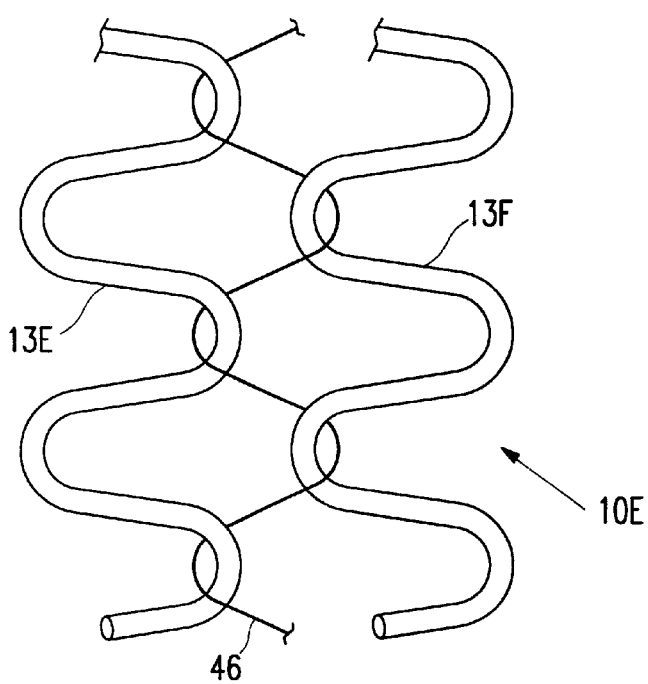
FIG. 7
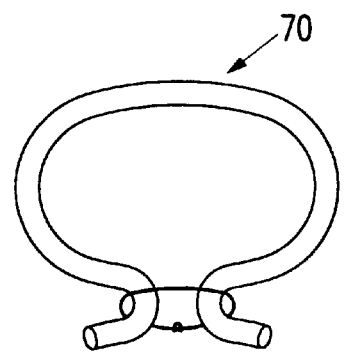
FIG. 8
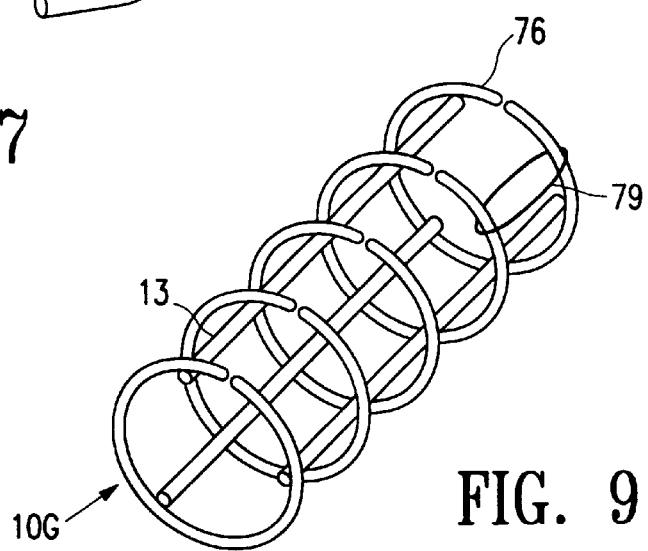
FIG. 9

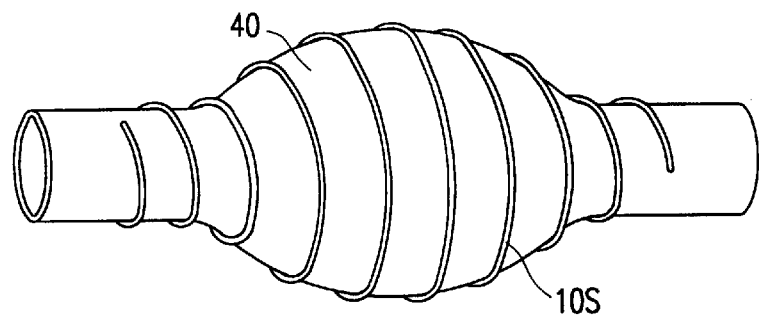
FIG. 63
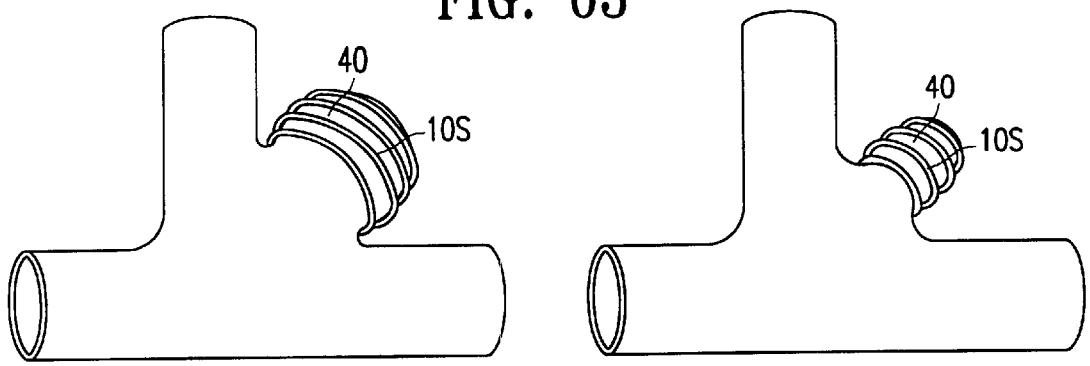
FIG. 64A           FIG. 64B
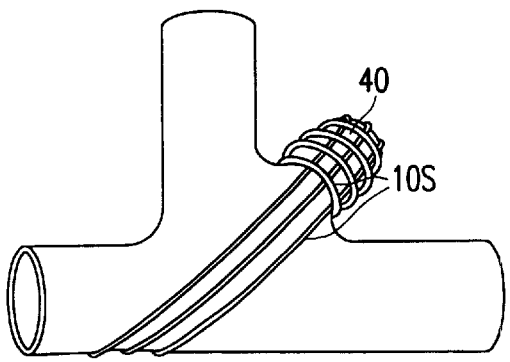 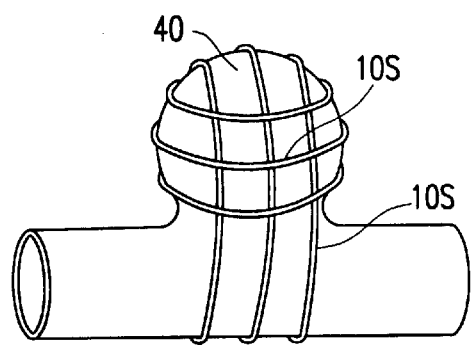
FIG. 64C           FIG. 65A
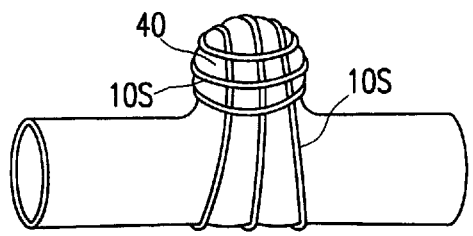 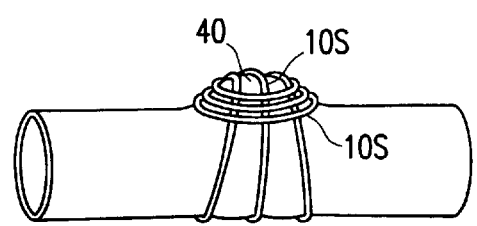
FIG. 65B           FIG. 65C

METHOD AND DEVICE FOR THE TREATMENT OF VULNERABLE TISSUE SITE

FIELD OF INVENTION

This invention relates to the fields of intervention, surgery, and more particularly to method and apparatus for treatment of aneurysms.

BACKGROUND OF THE INVENTION

An aneurysm is a condition in which a portion of a vessel has a weakened wall that results in the expansion of the vessel due to internal pressures. Aneurysm may be an aortic aneurysm occurring in the abdominal area or in other areas, including but not limited to: aneurysm in the thoracic aorta and neurovascular aneurysms.

Aortic aneurysm results from abnormal dilation of the artery wall and is often associated with arteriosclerotic disease. Unless treated, an aneurysm can rupture, leading to severe and often fatal hemorrhaging. Treating an aortic aneurysm generally involves transplanting a prosthetic graft to bridge or bypass the affected portion of the aorta. Surgical implantation of the graft is possible but this treatment causes considerable trauma, results in high mortality and morbidity and, even when completely successful, requires a lengthy recuperation period. Due to the difficulty of the operation, surgical replacement is even less attractive when it must be performed on an emergency basis after the aneurysm has ruptured.

A less invasive alternative involves the use of a catheter for intraluminal delivery of a graft. Graft delivery systems can employ a graft with expandable portions that anchor the graft in the aorta. Often, the systems use an inflatable balloon on the delivery catheter to expand the anchoring portion of the graft as disclosed in U.S. Pat. No. 5,275,622 (Lazarus et al.) which is hereby incorporated in its entirety by reference thereto. This latter example requires the use of a bulky capsule to store the graft and a complicated pushrod system to deploy the graft.

The success of a percutaneous vessel repair depends in large part on getting the graft to the location of the vasculature in need of repair and deploying the graft effectively. A difficulty associated with graft deployment and its effectiveness is blood flow-by which occurs when blood can pass between the graft and the patient's vessel wall, bypassing the graft.

Although the referenced prior art systems and others employ many different stent and graft configurations, the limitation of complete aneurysm containment has not been met.

These systems are frequently too bulky and inflexible to access many regions of a patient's vasculature. In addition when using endovascular stent grafting, it is important to know the diameter, length, and healthy neck length segment of the aneurysm in order to prevent perigraft leaks caused by poor arterial apposition or by foreshortening of the endovascular graft.

In the neurovascular applications, a particular example for aneurysm repair is the treatment of an aneurysm by placing radiopaque materials within an aneurysm pouch. For example, it is known to push embolic coils through an introducer catheter. However, once the embolic coils leave the introducer catheter they are no longer under control and may become repositioned away from the desired location. This might occur, for example, when the treatment site is located near a vessel having a larger lumen, as when the embolic coil, having migrated to the larger vessel, would travel to a remote location. Other disadvantages include the possibility of the coils rupturing the wall of the aneurysm sac or the further expansion of the aneurysm.

Another example of vulnerable tissue sites other than aneurysms include vein grafts implanted as a bypass graft in CABG procedures. A disadvantage of a vein graft is that it may degrade over time as a result of the vein structure not being adept to effectively handle high arterial pressure (e.g., being a weaker structure against pressure), thereby degrading and occluding over time. Typically, by the time intervention takes place, the vein graft has degraded or occluded thus making it difficult to salvage or treat.

Thus, what has been needed is a method and device that can provide less invasive and more effective treatment of vulnerable tissue sites, in particular arterial and other aneurysms. The present invention satisfies at least some of this and other needs.

SUMMARY OF THE INVENTION

The present invention is directed to a method and apparatus for treating vulnerable tissue sites such as aneurysms in the abdominal or thoracic aorta. Other applications of for the method and apparatus of the present invention include neurovascular aneurysms, veins, vein grafts, and expanded or thinned tissues on various organs and body surfaces.

The apparatus of the present invention, is directed to containment members for at least partially containing a vulnerable tissue site, thus preventing or minimizing the further vulnerability or growth of the site. Additionally, or alternatively, the containment members can apply resistive force to the vulnerable tissue site. The force can be compressive against the exterior surface of the tissue site. The containment members of the present invention can be used alone or in combination with support members, such as stent/grafts, in treating a tissue site. In this embodiment, the support member is disposed within the inner lumen of the vulnerable tissue site with the containment member disposed on the exterior surface of the lumen.

The containment members may totally encircle the vulnerable tissue site or they may be disposed about less than the entire circumference of body lumen including the vulnerable tissue site. In one embodiment, the containment members have a containment surface of sufficient dimensions to at least partially encircle a region of the vulnerable tissue. In another embodiment, the containment member can be configured to provide a compressive force against the vulnerable tissue. The containment members may be configured for attachment to a positioning member. The positioning member can be configured for securing the containment member to an adjacent tissue site or body part to minimize further vulnerability of the tissue site. In another embodiment, the positioning member is configured to be biased against an adjacent healthy tissue site or body part.

The various embodiments of the containment members of the present invention can be configured to deliver agents, such as therapeutic agents, to the tissue site. Additionally, the containment members can be configured to accommodate different anatomical settings having vulnerable tissue sites. The embodiments include but are not limited to strands, coils, sheaths, omega shaped coils for structures that can not be looped around entirely, and inflatable containment members.

The containment member may be formed of polymeric or metallic material to remain in place until the removal of the same, or in the alternative may be formed of biodegradable material, degrading over a period of time.

In operation, the containment members of the present invention may be introduced to the vulnerable tissue site in one of several ways, including: (1) surgical methods, such as cut-down or laparoscopically; (2) intra-endoscopically, i.e., through the same body conduit or lumen as the one including the vulnerable tissue; and (3) inter-endoscopically, i.e., through, at least in part, a body conduit or lumen adjacent the conduit which has the vulnerable tissue.

In one embodiment, the containment member is advanced through the first lumen of the first tubular member including the vulnerable tissue site and through an access site in a wall of the first tubular member and is disposed about an exterior surface of the tissue site.

In another embodiment, the access site is part of a second tubular body member having a second lumen and disposed, at least in part, substantially parallel and adjacent the tissue site. In this embodiment, the containment member is advanced through the second tubular body and through the access site located in a wall of the second tubular body and disposed about an exterior surface of the tissue site. The containment member can be disposed about the exterior surface of the first body lumen which includes the vulnerable tissue site alone or together with the exterior surface of the second body lumen.

As defined herein, vulnerable tissue site includes, without limitation, any tissue site which is or can be weakened, enlarged, thickened, or thinned, either permanently or periodically (as for example during different phases, cycles, or conditions). The vulnerable tissue may be present in any area of a host body, such as but not limited to: cardiovascular or neurovascular arteries or veins, vein grafts such as saphenous vein graft for a pass surgery, aorta including abdominal and thoracic, vena cava including inferior and superior, organs such as stomach or glands. The vulnerable tissue site may be native to the intracorporeal body or it may be a transplanted intracorporeal body such as a saphenous vein graft introduced to the body as a result of a procedure such as bypass before it becomes weakened as a result of its new environment.

BRIEF DESCRIPTION OF THE DRAWINGS

FIGS. 6A–6C are transverse cross sectional views of containment members embodying features of the present invention and having different cross-sectional shapes.

FIG. 7 is an elevational view of another embodiment of a containment member having a double helix configuration.

FIG. 8 is an elevational view of a an omega shaped containment member.

FIG. 9 is an elevation view of another embodiment of a containment member including longitudinal strands with transverse connecting member.

FIGS. 63–65 are schematic side elevational views of the containment members embodying features of the present invention and disposed about the outer surface of host body such as an organ, showing the reduction in size of the organ at the vulnerable tissue site, immediately, over time, or at phase intervals.

DETAILED DESCRIPTION OF THE INVENTION

Figure 1:
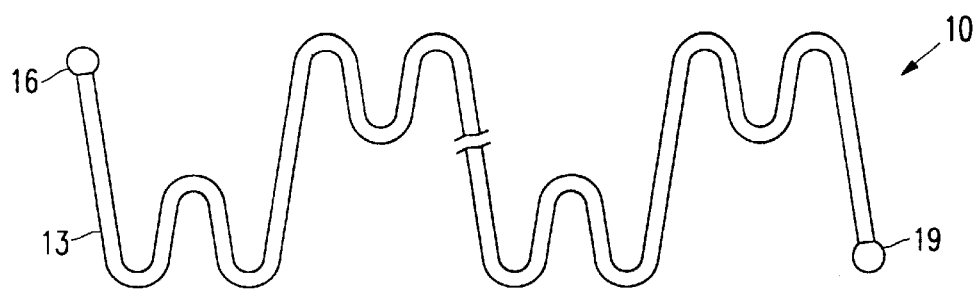
FIG. 1 is an elevational view, partially cut away view of a containment member embodying features of the present invention.
Figure 2:
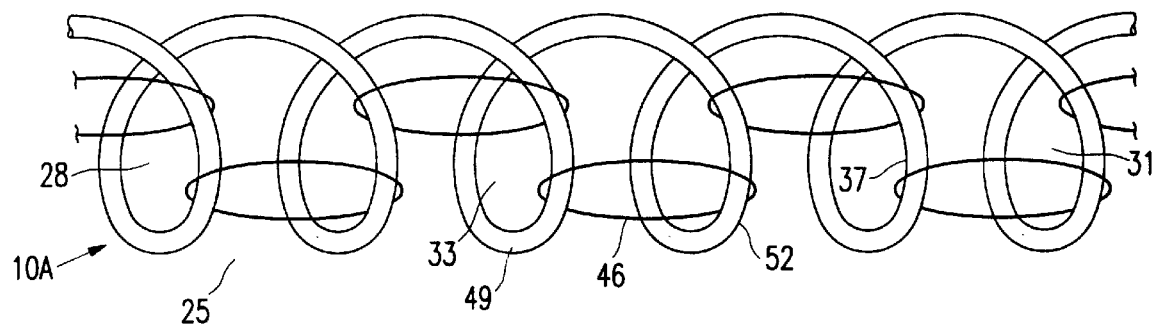
FIG. 2 is another embodiment of a containment member embodying features of the present invention taking the form of a coil.

FIGS. 1 and 2 illustrate containment members 10 and 10A embodying features of the invention, generally including a strand 13, preferably having atraumatic proximal and distal tips, 16 and 19. The containment member 10, preferably, is wound in a helical configuration as generally depicted as 10A in FIG. 2. The containment member 10 forms, as in containment member 10A of FIG. 2, or, can be shaped to form, a tubular body 25 having open proximal and distal ends, 28 and 31, respectively, with a containment lumen 34 extending longitudinally therebetween, and defining an interior surface 37.

Figure 3A:
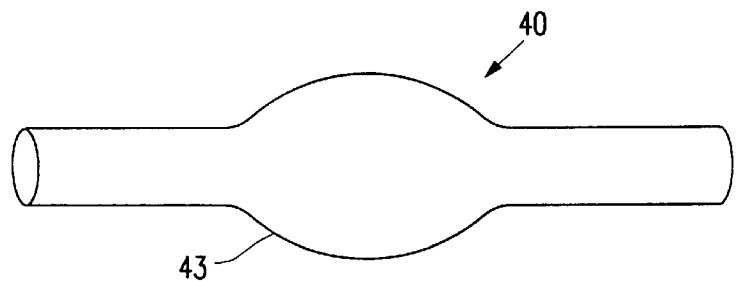
FIG. 3A is a side elevational view of a vulnerable tissue site.
Figure 3B:
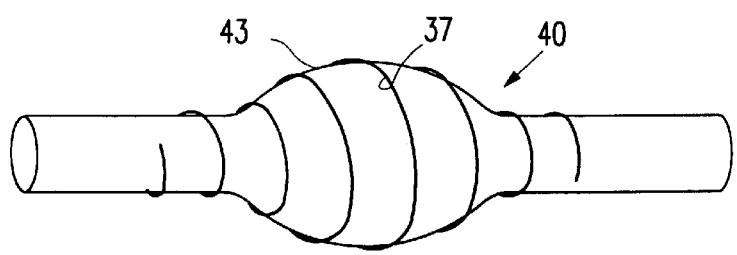
FIG. 3B is a side elevational view of the vulnerable tissue site of 3A having the containment member disposed about its exterior surface.

Upon disposing of the containment member 10 about a vulnerable tissue site 40, such as that shown in FIGS. 3A and 3B, the interior surface 37 of the containment member 10 comes into contact, at least in part, with an exterior surface 43 of the vulnerable tissue site 40, thus containing, at least in part, the vulnerable tissue site. In one embodiment, in the disposed configuration, the containment member 10 can apply resistive force to the tissue site, aiding in the minimizing the further vulnerability of the vulnerable tissue site. The containment member 10 can also apply a compressive force against the exterior of the vulnerable tissue. The strand 13 may be formed of any suitable material such as polymeric or metallic materials, including thermoplastic and thermosets; stainless steel, nickel titanium alloys such as Nitinol, and precipitation hardenable material. The precipitation hardenable material, preferably, is formed of at least two material selected from the group consisting of nickel, cobalt, molybdenum, chromium, tungsten, and iron; and a combination thereof.

Specific example of such precipitation hardenable material include, but are not limited to, AISI (American Iron and Steel Institute) Type 600 series precipitation hardenable stainless steel; chromium-nickel based single stage martensitic precipitation hardenable stainless steel having modified proportions of chromium and nickel and with additional elements of copper and titanium, commercially available from Carpenter Steel Company of Reading, Pa., under the designation 455PH or 17-7PH; and a precipitation hardenable steel available under the trade designation 1RK91 from Sweden Steel. Other suitable precipitation hardenable stainless steel include those which are essentially "nickel free" such as those sold under the designation BioDur 108, available from Carpenter's Specialty Alloys Operations, Reading, Pa. By way of example, the nominal composition of BioDur is chromium (21%), manganese (23%), nitrogen (1%), nickel (less than 0.3%), and iron (balance).

Other suitable precipitation hardenable material include cobalt based alloys such as those including nickel, cobalt, molybdenum and chromium, also commercially available under the designation MP35N (UNS (Unified Numbering System) R30035) available from Carpenter Steel Co. Also useful in the practice of the invention is a similar alloy that contains a small amount of iron (less than about 10%) and is commercially available under the trade designation Elgiloy (UNS R30003) and L605 from Haynes International of Kokomo, In.

Alternatively, the strand 13 may be formed of biodegradable material, preferably degrading over a period of time, as for example few days to years, preferably within 1 to 10 months. The biodegradable material may be formed from any suitable bio-compatible material such as, but not limited to: enzymatically degradable polymers including polypeptices such as collagens, gelatin, poly(amino acids); polysaccharides such as amylose cellulose, dextran, chitin; polyesters such as poly(β-hydroxyalkanoates), pHB (poly β-hydroxybutyrate); and nucleic Acids; or nonenzymatically degradable polymers, including, polyesters such as aliphatic polyesters, as for example, PLA (polylactic acid), PGA (polyglycolic acid), co-polymer of PLA/PGA; poly(ester-ethers) such as PEG (poly(ethylene glycol)); poly caprolactones; and poly (amideesters).

As defined herein, vulnerable tissue site refers to any tissue site which is or can be weakened, enlarged, thickened, or thinned, either permanently or periodically (as for example during different phases, cycles, or conditions). The vulnerable tissue may be present in any area of a host body, such as but not limited to: cardiovascular or neurovascular arteries and veins, aorta including abdominal and thoracic, vena cava including inferior and superior, organs such as stomach or glands, and vein grafts.

The containment member 10 and other embodiments of the same, will be further discussed in reference to the figures below, wherein like reference represent like elements.

Optionally, and as shown in FIG. 2, the containment member 10, can, optionally, include, one or more connecting bodies 46, for connecting adjacent turns 49 and 52 of the containment member.

The containment member 10 for aortic aneurysms, preferably, has a disposed inner diameter ranging from about 0.25 to about 4 inches, more preferably, from about 0.75 to about 2.5 inches; with a disposed outer diameter ranging from about 0.27 to about 5 inches, more preferably, from about 0.77 to about 2.6 inches; and a disposed length ranging from about 1 to about 30 cm (with a straight length ranging from about 1 to about 50 cm), more preferably, from about 5 to about 20 cm. However, the containment member 10 inner and outer diameters and length may vary in size from those stated above for other applications and size of the vulnerable tissue site on which the containment member 10 is to be disposed.

For example, the containment member in a disposed but unstrained (or relaxed) condition can have an inner diameter substantially the same or slightly larger than a first thickness (outer diameter of the tissue site) of the vulnerable tissue site; substantially larger than the thickness of the vulnerable tissue site; about 25% larger than the thickness of the vulnerable tissue site; substantially between the first thickness of the vulnerable tissue site and second thickness of a healthy tissue site adjacent the vulnerable tissue site; substantially the same as the second thickness of the adjacent tissue site; or slightly smaller, for example 10% smaller than the second thickness of the adjacent tissue site. Adjacent tissue site, as used herein, refers to a tissue site which is adjacent the vulnerable tissue site and is substantially healthy, or adjacent body part, including but not limiting to tissue sites, bones, organs, etc.

The containment member 10A, preferably, has a pitch (distance between adjacent turns), ranging from about 0.01 to about 3 inches, more preferably, from about 0.04 to about 1 inch.

Figure 4A:
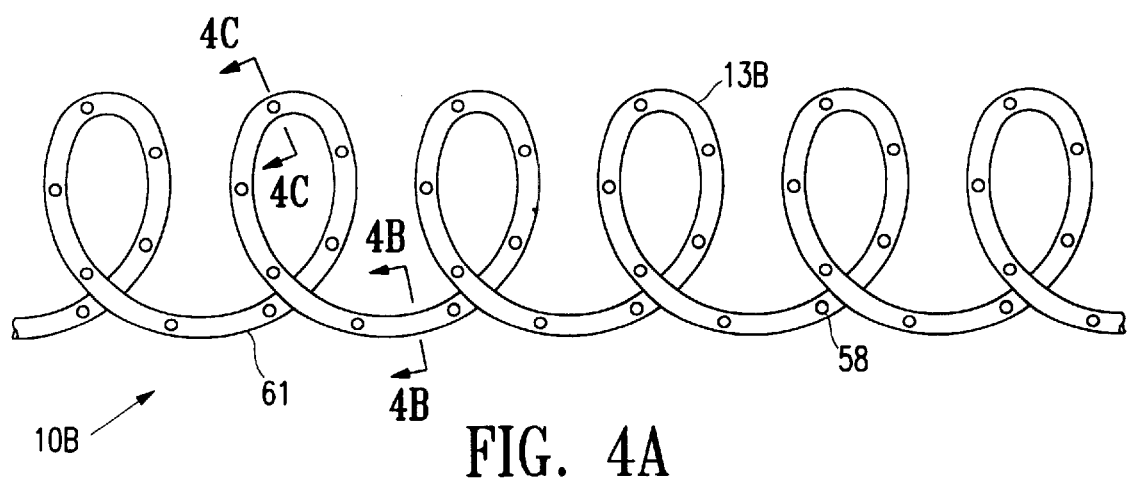
FIG. 4A is a side elevational view of an embodiment of the containment member of FIG. 2 including apertures.
Figure 4B:
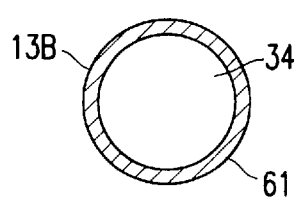
FIG. 4B is a transverse cross-sectional view of the containment member of FIG. 4A taken along lines 4B—4B.
Figure 4C:
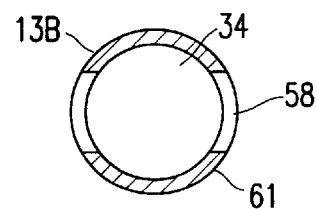
FIG. 4C is a transverse cross-sectional view of the containment member of FIG. 4A taken along lines 4C—4C.

In an embodiment features of which are shown in FIGS. 4A through 4C, the containment member 10B is formed of a hollow strand 13B having a strand lumen 34 extending therein, and further including one or more apertures 58 extending between the lumen 34 and an strand outer surface 61. The strand lumen 34, and the apertures 58 when present, are configured to deliver fluids, such as therapeutic fluids, to and/or from the vulnerable tissue 40. Optionally, the apertures 58 may be used to deliver a hardenable material, including bio-degradable and permanent materials, preferably, bio-degradable over time (such as those described above in reference to strand material) to the outer surface of the vulnerable tissue site. In yet another embodiment, the hardenable material may be delivered to the exterior surface of the vulnerable tissue site by another delivery device, such as a catheter. It should be appreciated that the delivery of the hardenable material can occur, after, concurrently with, or prior to the placement of the containment member on the vulnerable tissue site. In yet another embodiment, the hardenable material itself can be the containment member left in place permanently, or degradable over time. In this embodiment, the containment member can take any suitable shape necessary for at least partially containing the vulnerable tissue site.

Figure 5A:
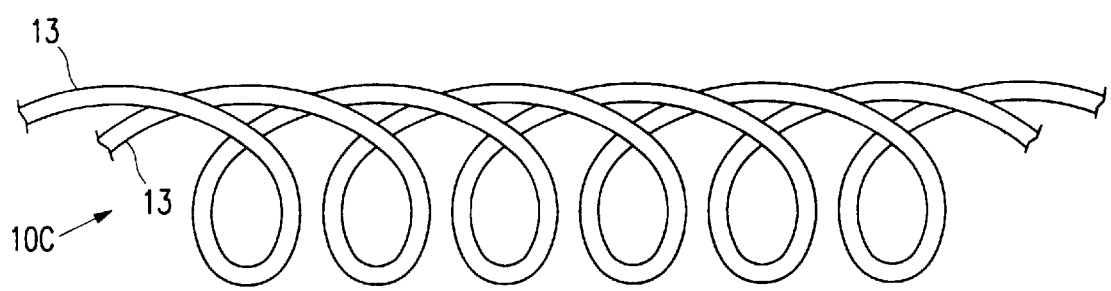
FIG. 5A is another embodiment of a containment member embodying features of the present invention and having a plurality of strands and having a circular cross section.
Figure 5B:
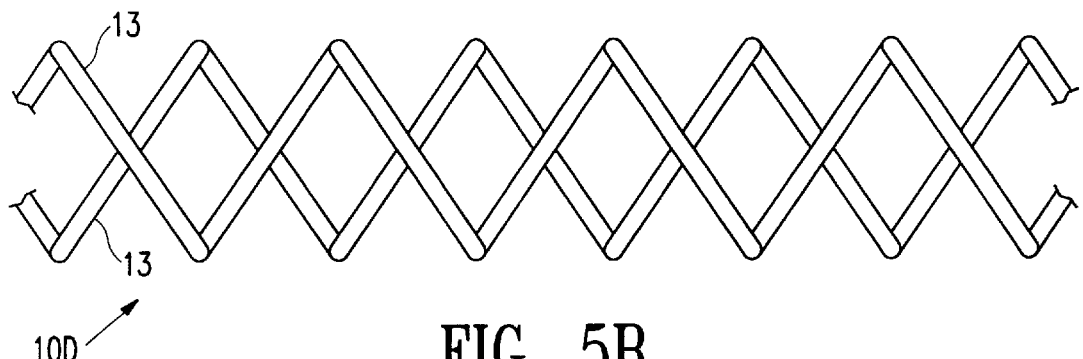
FIG. 5B is another embodiment of a containment member embodying features of the present invention and having a plurality of strands having a flat cross section.

Now referring to FIGS. 5 through 6, the containment member 10, is generally shown in 10C and 10D respectively and includes a plurality of strands 13, 5A in-phase and 5B out of phase, having varying cross sections, as for example, substantially circular as shown in FIG. 6A, substantially flat as in FIG. 6B, substantially triangular as in FIG. 6C, or other shapes as dictated by a particular application or anatomy.

In another embodiment shown in FIG. 7, the containment member 10E includes a multiple helix configuration having two counter helix strands 13E and 13F. The strands 13E and 13F can have identical or differing diameters (inner and/or outer). The counter helix strands 13E and 13F forming the double helix containment member 10E can interlock by alternating inner and outer positions as shown in FIG. 7. Optionally, the proximal and distal ends of the counter helix strands 13E and 13F, or portions along their length, can be joined by suitable means, such as connecting member 46 as shown in FIG. 7, and means in the form of a ring 70 as shown in FIG. 8.

Also, the embodiment shown in FIG. 8, can be a containment member having a omega shape for containing vulnerable tissue sites, such as those attached to other tissue and or organs such as bones. One or more omega shaped containment members loops, at least partially, around the vulnerable tissue site, thus containing the site. The legs of the containment member can be affixed or secured to the vulnerable tissue site, or an adjacent structure such as a bone, with adhesive, staples suture, or strand; or when multiple containment members are used, each leg can be connected to a leg of another containment member.

Now referring to FIG. 9, the containment member 10G includes a plurality of longitudinal strands 13 transversely set apart, with transverse connecting member 76 disposed about the inner or outer surface of the longitudinal strands 13 securing the relative position of the longitudinal strands 13. The transverse connecting member 76 may be only secured to the corresponding underlying longitudinal strands 13, or they may be additionally linked to one another through linking member 79. Transverse connecting member 76 and linking member 79 can, independently, be made of any suitable material such as those described above with reference to the strand 13.

Now referring to FIGS. 10 through 16, containment members of the present invention described above may further include one or more sheets disposed around the exterior surface of one or more strands.

Figure 10:
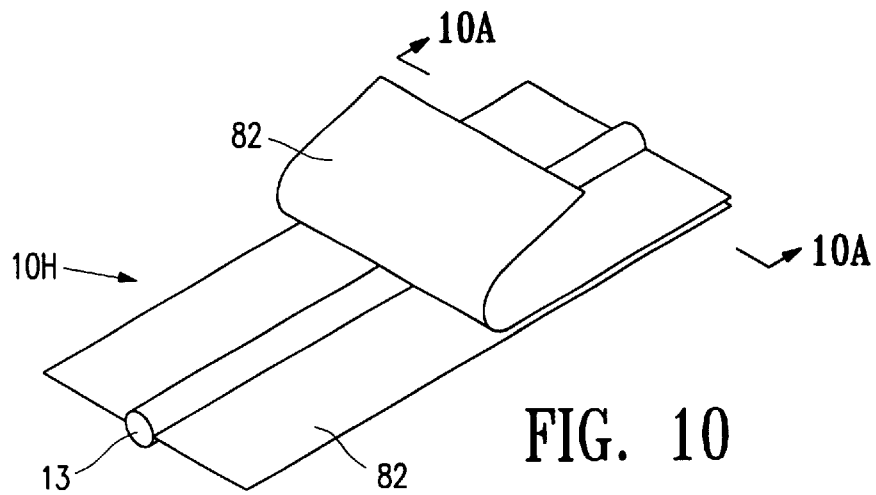
FIG. 10 is an elevational view of a containment member including two sheets disposed around the exterior surface of a strand.
Figure 10A:
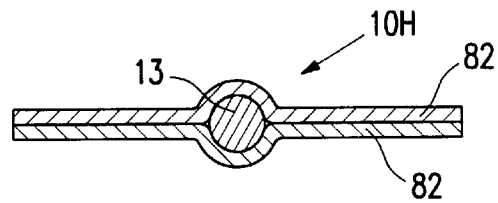
FIG. 10A is a cross sectional view of the containment member of FIG. 10 taken along lines 10A—10A.
Figure 11A:
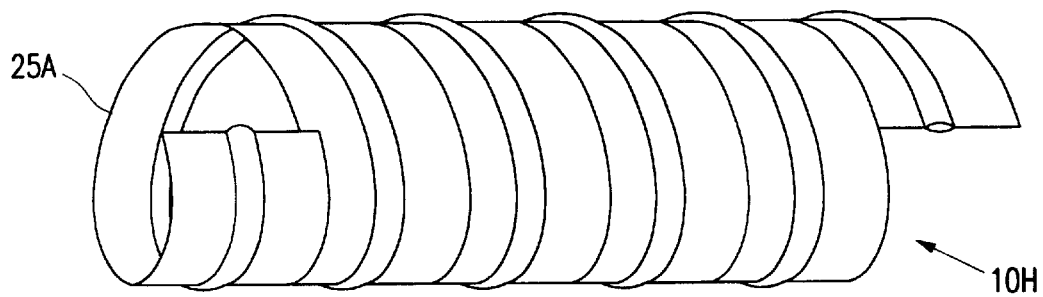
FIGS. 11A and 11B are side elevational views of the containment member of FIG. 10 in a disposed configuration.
Figure 11B:
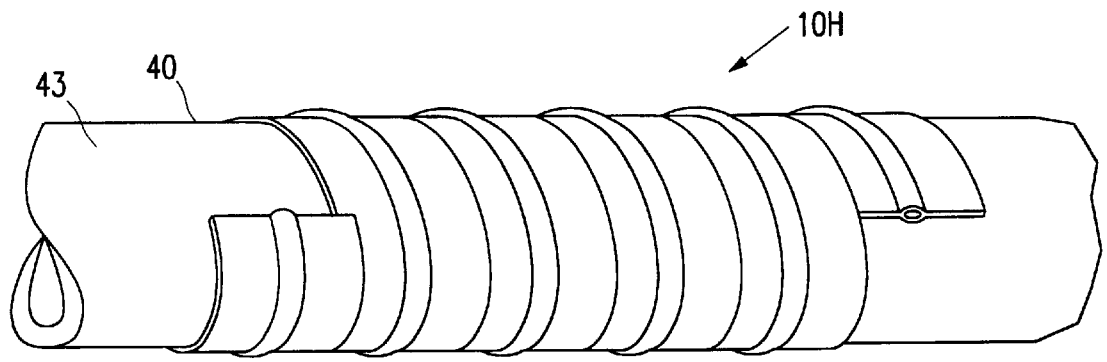
Figure 11C:
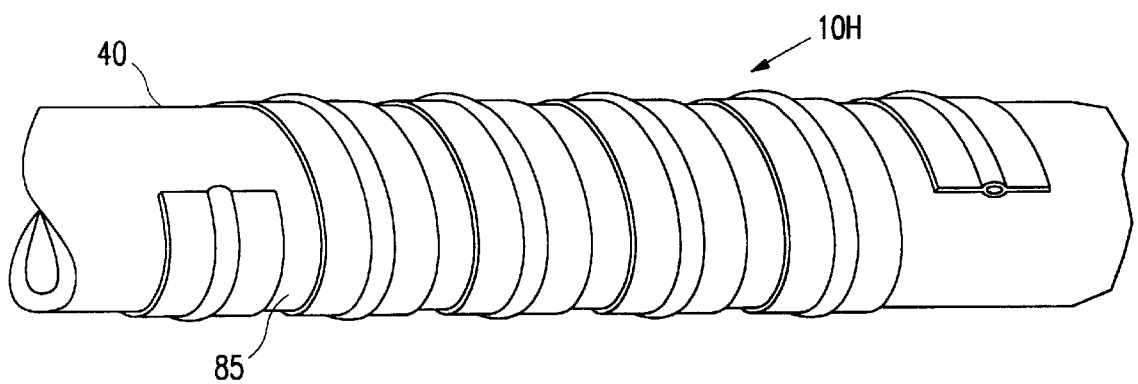
FIG. 11C is a side elevational view of the containment member of FIG. 10 disposed around the exterior surface of a body lumen with the edges of the containment member being longitudinally set apart.

In the embodiment shown in FIGS. 10 and 10A, an enlarged section of a containment member 10H is shown having a strand 13 sealingly disposed between two sheets or strips of film or mesh 82. Optionally, the exterior surface of one or more of the strips of film, or any strand or containment member, can include a securing material such as a adhesion promoting material or time-release adhesive, such as fibrin or cyanoacrylate, to aid in securing the containment member 10H to the outer surface 43 of the vulnerable tissue 40. As shown in FIGS. 11A through 11C, after the containment member 10H is disposed about the vulnerable tissue, per the method described below, the containment member 10H forms, preferably, a helical configuration with the edges of the attached films 82 overlapping, to form a tubular structure 25A. When only one of the films includes the securing material, the containment member 10H is, preferably, disposed about the exterior of the vulnerable tissue site 40 such that the side having the securing material comes into contact, at least in part, with the outer surface 43 of the vulnerable tissue site 40. Alternatively, and as shown in FIG. 11C the edges of the containment member 10H may be longitudinally set apart by a gap 85.

Figure 12:
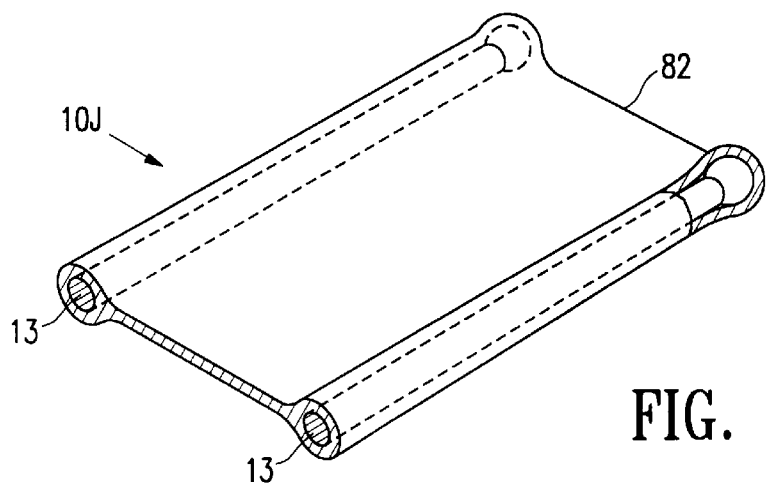
FIG. 12 is an elevational view of another embodiment of a containment member including a plurality of strands disposed substantially parallel to one another and sealed between two sheets.
Figure 13:
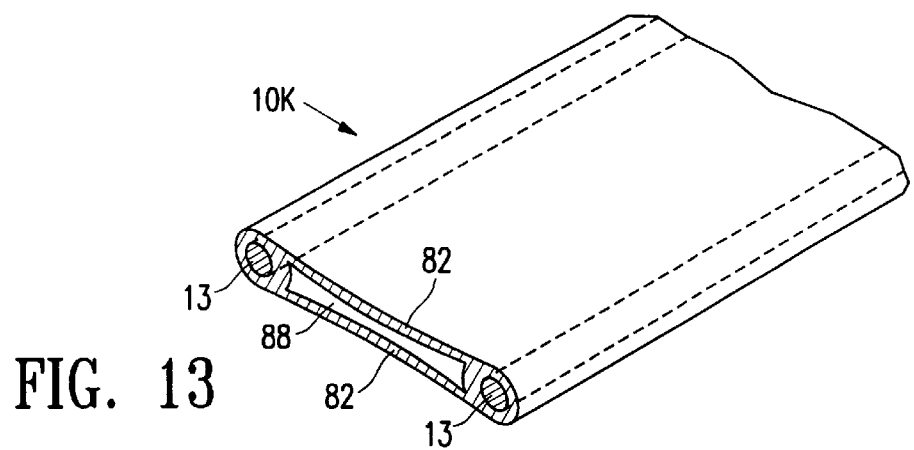
FIG. 13. is an elevational view of another embodiment of the containment member of FIG. 12 including an inflation pocket defined between the two sheets.

In an alternate embodiment, an enlarged section of a containment member 10J prior to being disposed about the vulnerable tissue is shown in FIG. 12. A plurality of strands 13 of the containment member 10J are disposed substantially parallel to one another and are sealed between two sheets or strips of film or mesh 82, as described above in relation to FIG. 10. Alternatively, as shown in FIG. 13, in containment member 10K, the two films 82 together define an inflation pocket 88 sealingly and fluidically connectable to a source of inflation fluid. Once the containment member 10K has been disposed about the vulnerable tissue site 40, the inflation pocket 88 can be used to inflate, with a fluid (liquid or gas), the containment member 10K thus exerting pressure on the vulnerable tissue site 40.

Figure 14:
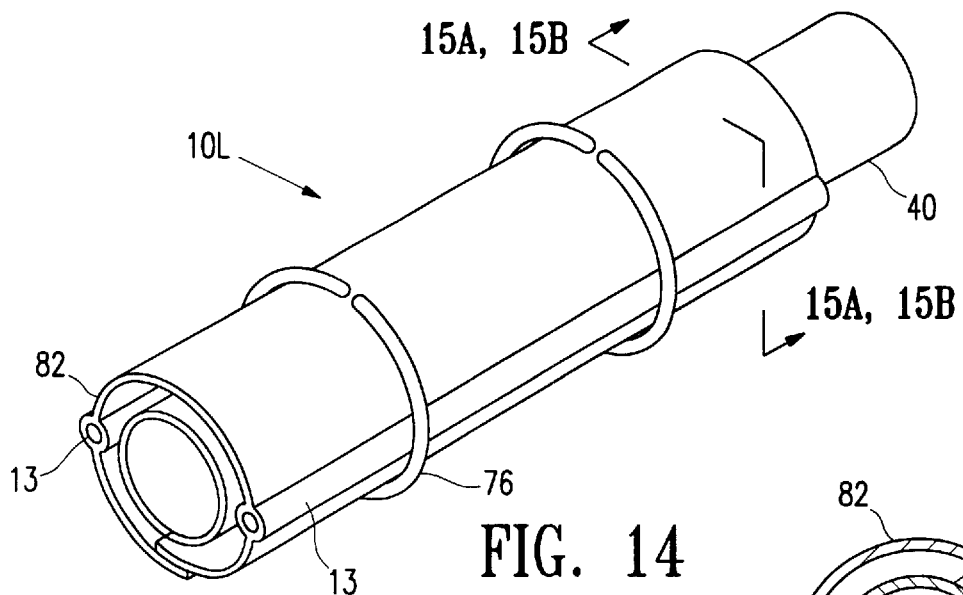
FIGS. 14, 15A and 15B are side elevational views of containment members including sheets disposed about longitudinal strands and further including transverse connecting member, the longitudinal strands having solid or hollow cross-sections.
Figure 15B:
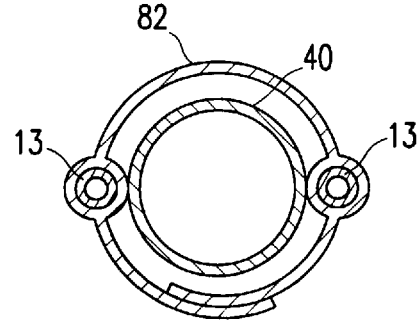
Figure 15A:
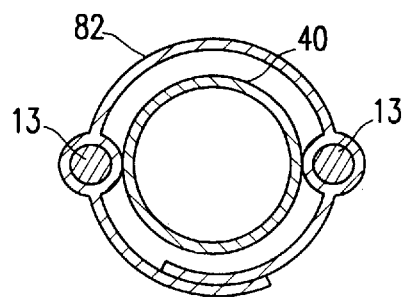

In another embodiment shown in FIGS. 14, 15A and 15B, an enlarged section of a containment member 10L is shown having longitudinal strands 13 disposed between two sheets or strips of film or mesh 82, with transverse connecting member 76 disposed on the outer or the inner sheets or therebetween. The longitudinal strands 13 may be solid or hollow (or have closed proximal and distal ends), as shown in FIGS. 15A and 15B, respectively.

Figure 16:
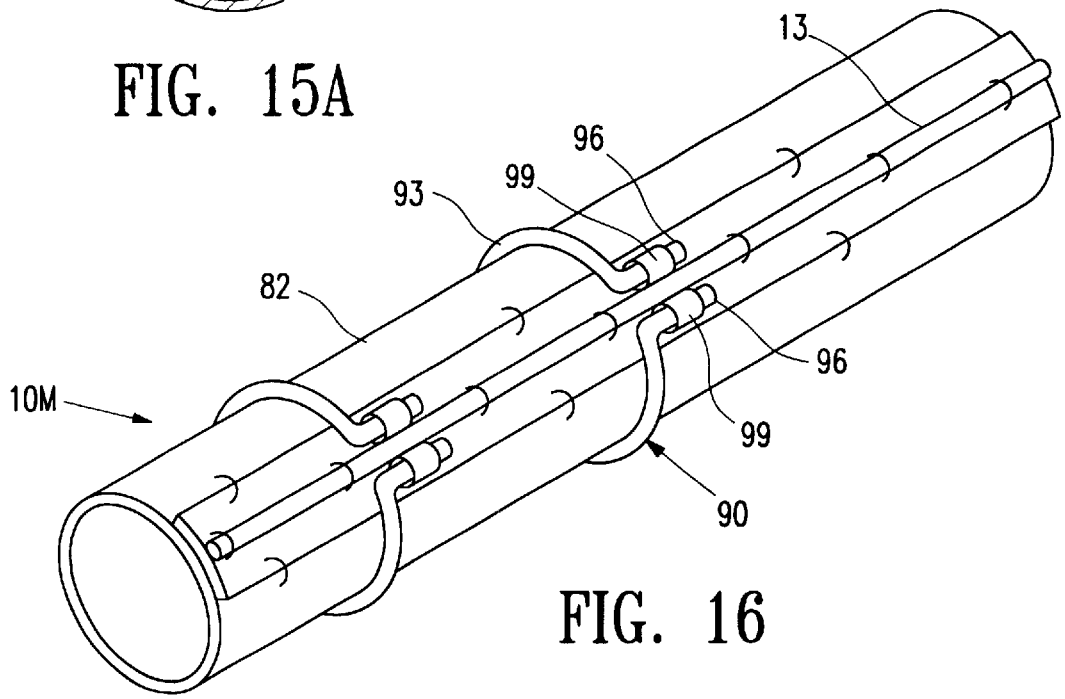
FIGS. 16–18 are side elevational views of different embodiments of transverse connecting.
Figure 17:
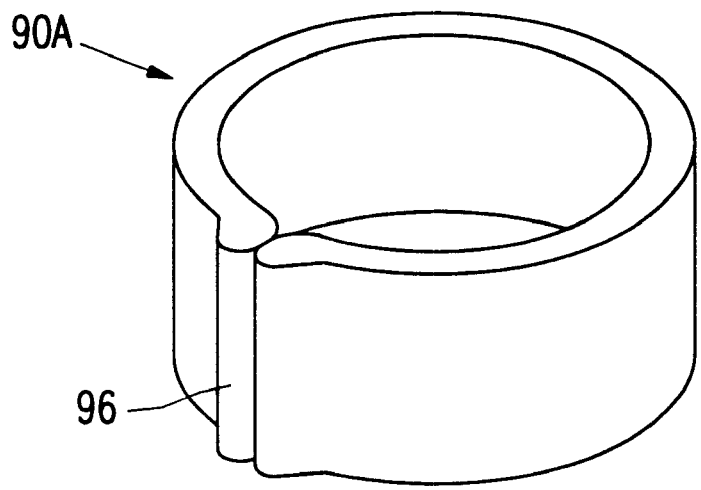
Figure 18:
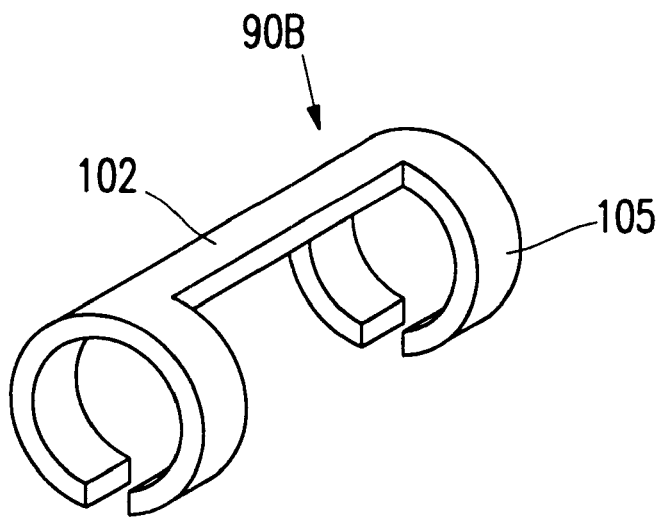

In another embodiment of a containment member 10M shown in FIG. 16, transverse connecting member 90 includes a generally annular body 93 averted ends 96 which may be used to secure the transverse connecting member 90 about the longitudinal strand 13. As shown in FIG. 16, the two averted ends 96 may be secured in place on either side of the longitudinal strand 13 in rings 99 located on an outer surface of the outer sheet 82. Alternatively, and as shown in FIG. 17, ends 96 of transverse connecting member 90A may hold sutures or other means for connecting the containment member to other containment members or tissue site. Alternatively, the member shown in FIG. 17 can itself be a containment member to be disposed about the vulnerable tissue site individually or in multiples (as discussed in reference to FIG. 8). In this embodiment, the containment member can be held in place by suitable means such as sutures In yet another embodiment as depicted in FIG. 18, transverse connecting member 90B can include a substantially longitudinal portion 102 with a plurality of encircling portions 105 for encircling the longitudinal strands.

Figure 19:
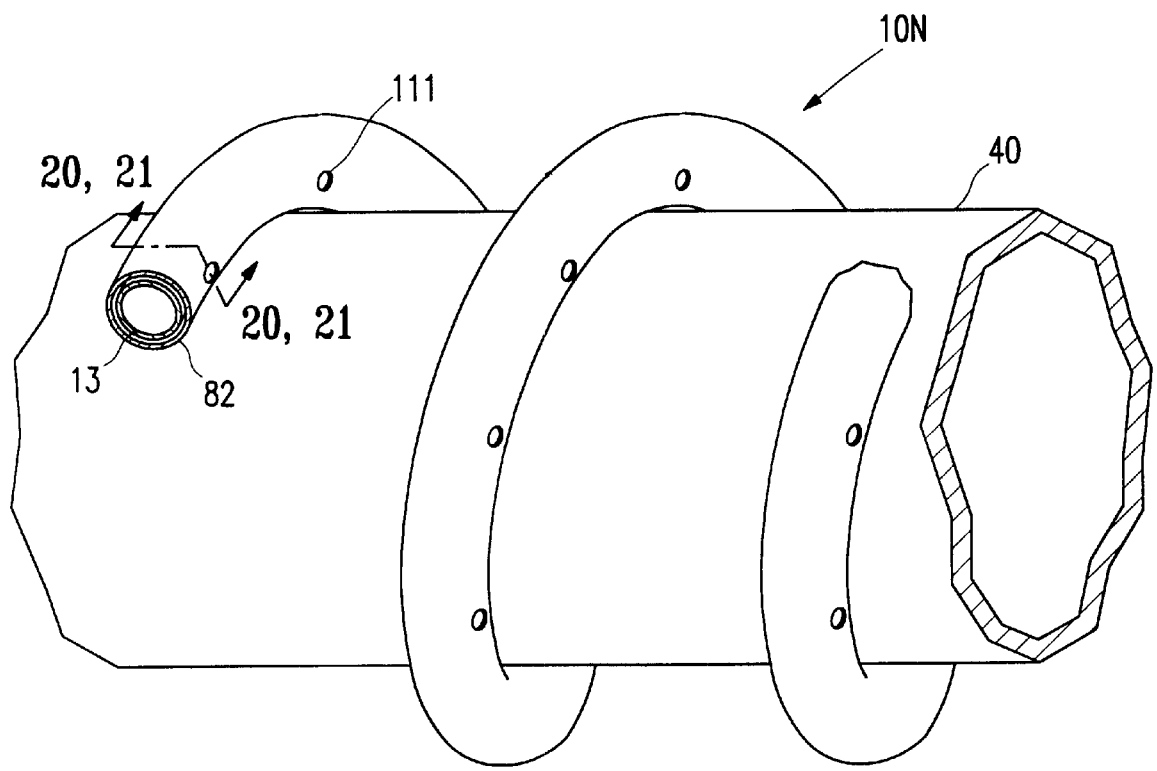
FIG. 19 is a side elevational view of a containment member having a fluid pocket.
Figure 20:
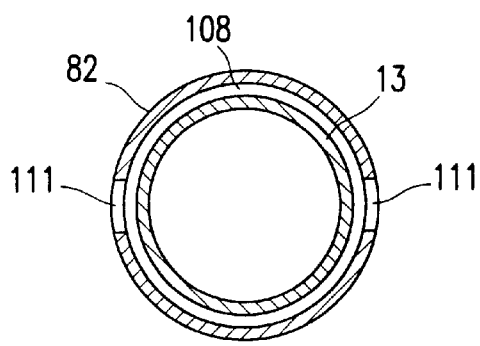
FIG. 20 is a cross sectional view of the containment member of FIG. 19 taken along line 20—20 with the strand being hollow.
Figure 21:
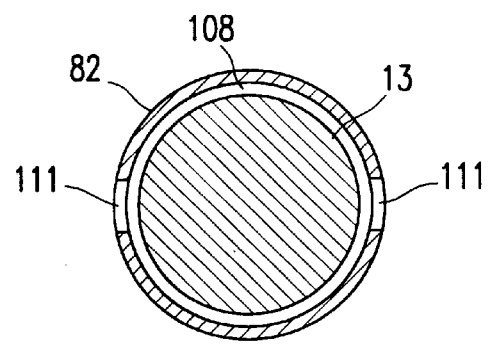
FIG. 21 is a cross sectional view of the containment member of FIG. 19 taken along line 21—21 with the strand being solid.

In another embodiment features of which are shown in FIGS. 19–21, containment member 10N includes a fluid pocket 108 defined between the outer surface of strand 13 and inner surface of sheath 82. The fluid pocket 108 is fluidically connectable to a source of therapeutic fluid for delivering the fluid to the vulnerable tissue and/or the surrounding tissue sites through sheath apertures 111 . The strand 13 may be hollow as shown in FIG. 20 or solid as shown in FIG. 21.

Figure 22A:
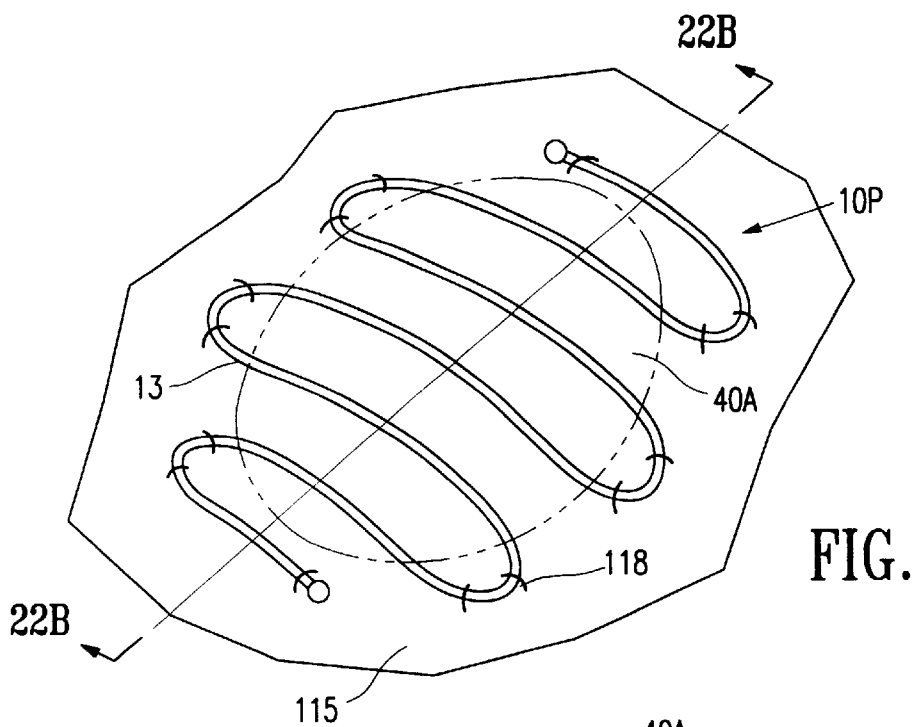
FIG. 22A is a top elevational view of a containment member disposed on an exterior surface a vulnerable tissue site being secured to a body tissue mass.
Figure 22B:
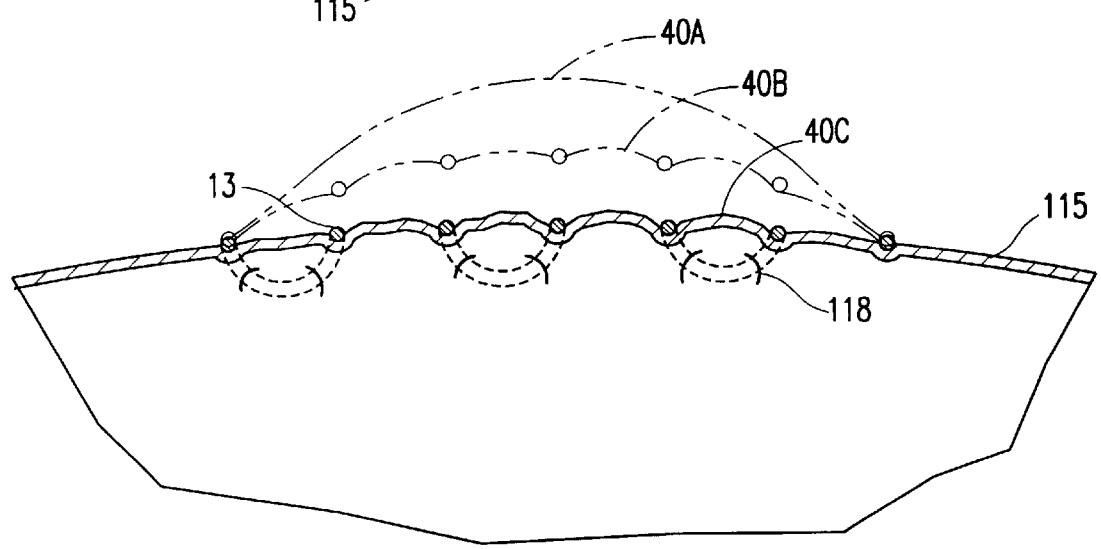
FIG. 22B is a side elevational view of the tissue site of FIG. 22A showing the reduction in size of the tissue site at different time or phase intervals.

Now referring to FIGS. 22A and B, features of a containment member 10P are shown containing a vulnerable tissue site 40A which is located on a body site 115 secured to body tissue mass. The containment member 10P includes strands 13 and is disposed about less than the circumference of the vulnerable tissue site 40A. The containment member 10P is secured to the vulnerable tissue site 40A or adjacent tissue site by sutures 118 or other suitable securing means. As shown in FIG. 22B, the containment member 10P may be used to apply pressure onto the vulnerable tissue site 40A, thereby reducing its size as it is reduced from 40A to 40B to 40C.

Figure 22C:
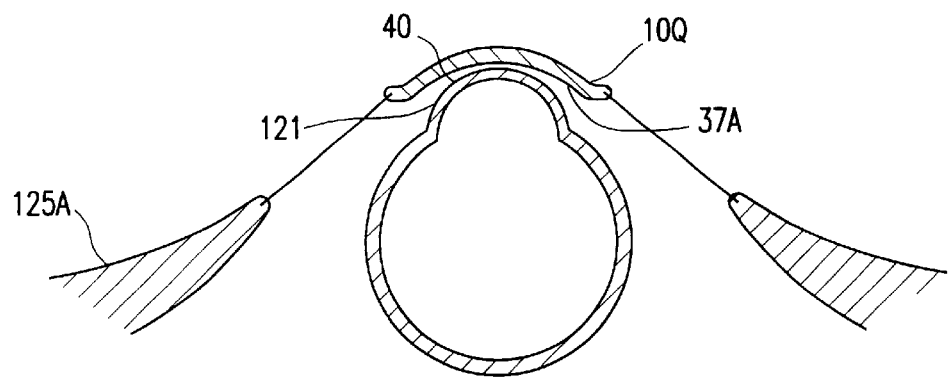
FIG. 22C is a front elevational view of a region of a vulnerable tissue site, with a containment member having a containment surface of sufficient dimensions to at least partially encircle the region of vulnerable tissue, the containment member being secured to adjacent healthy tissue by positioning member such as a suture.
Figure 22D:
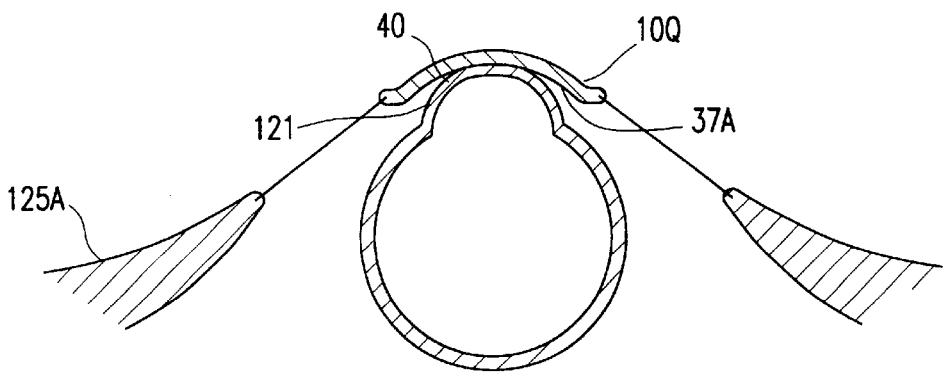
FIG. 22D is a front elevational view of a region of a vulnerable tissue site, with a containment member having a containment surface of sufficient dimensions to at least partially encircle the region of vulnerable tissue and being in substantial contact with the vulnerable tissue site, the containment member being secured to adjacent healthy tissue by positioning member such as a suture.
Figure 22E:
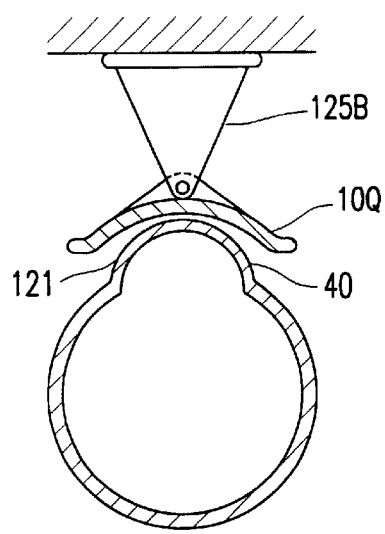
FIG. 22E is a front elevational view of a region of a vulnerable tissue site, with a containment member having a containment surface of sufficient dimensions to at least partially encircle the region of vulnerable tissue, the containment member being secured to adjacent healthy body part by positioning member such as a strut.
Figure 22F:
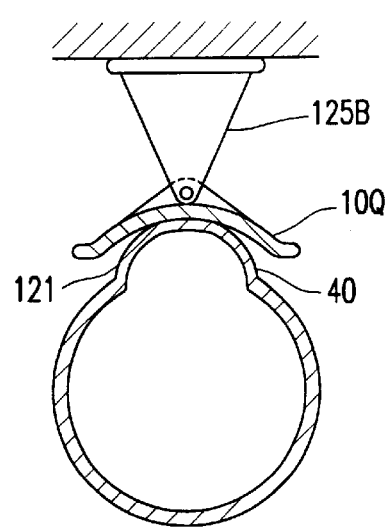
FIG. 22F is a front elevational view of a region of a vulnerable tissue site, with a containment member having a containment surface of sufficient dimensions to at least partially encircle the region of vulnerable tissue and being in substantial contact with the vulnerable tissue site, the containment member being secured to adjacent healthy body part by positioning member such as a strut.
Figure 24:
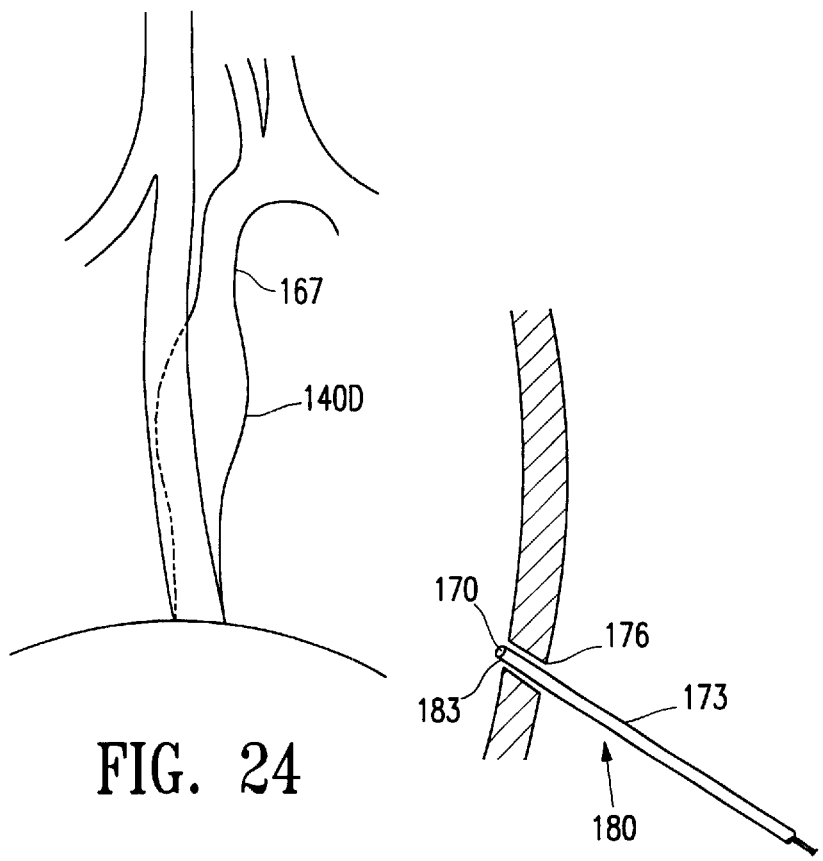
FIGS. 24–29 are schematic side elevational views of the steps of a surgical method of the present invention disposing a containment member about the exterior surface of a first body lumen including the vulnerable tissue site.
Figure 25:
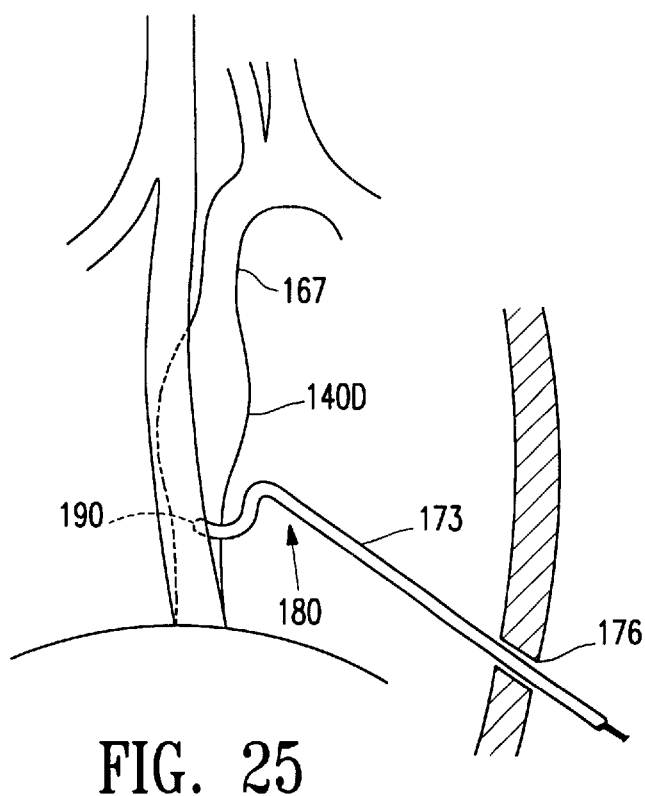
Figure 26:
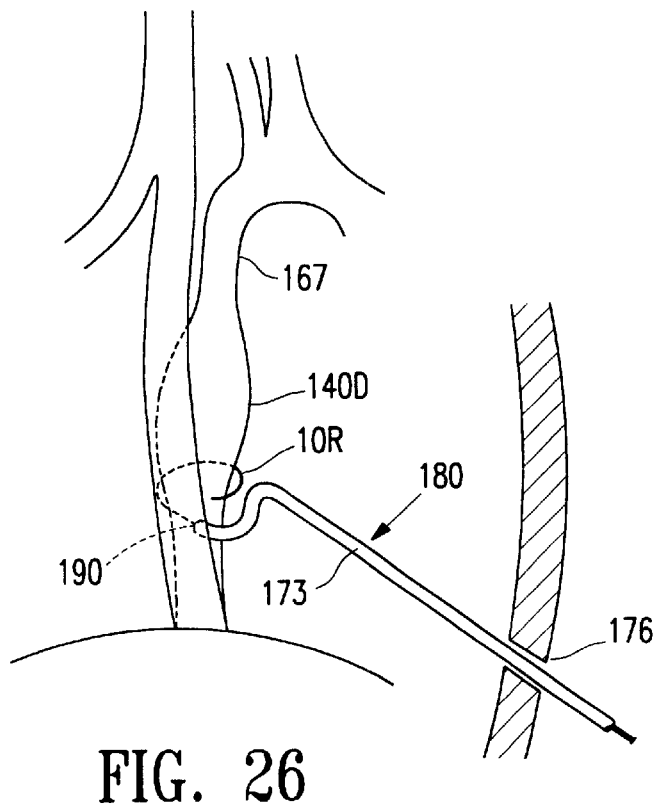
Figure 27:
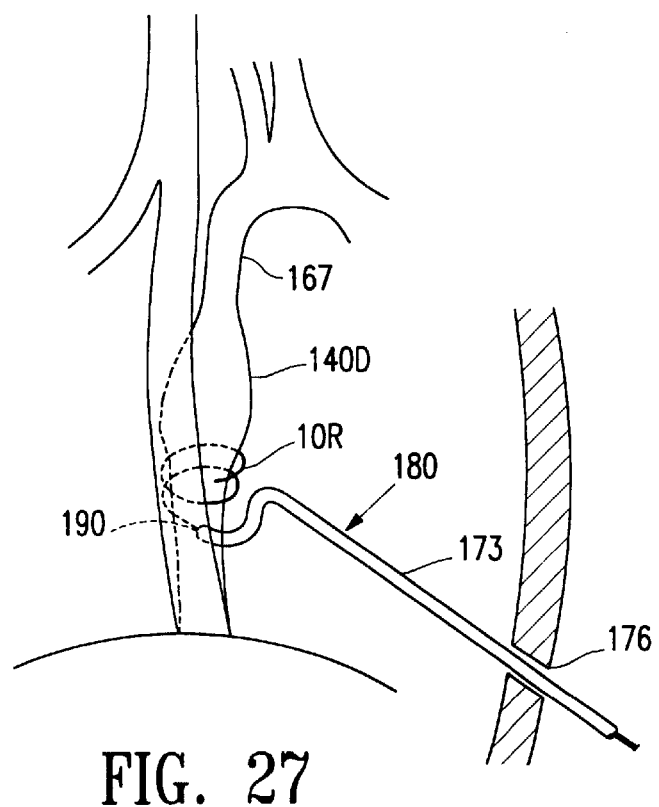

Now referring to FIGS. 22C–D and 22 E–F, the containment member 10R can have a containment member surface 37A of sufficient dimensions to at least partially encircle at least a region 121 of the vulnerable tissue 40. The containment member 10R is configured for attachment to a positioning member, such as 125A in the form of a suture or C ring, or 125B in the form of a strut. The containment members may be positioned to simply act as a means to minimize future vulnerability of the site (i.e., initially there is not substantial contact between the vulnerable tissue and the containment member), as for example depicted in FIGS. 22C & E; or to apply force against the vulnerable tissue (FIGS. 22D and F). As can be noted from the features of the embodiment shown in FIG. 22F, the containment member can be biased against adjacent healthy tissue site or body part (including bones).

In operation, the containment members of the present invention may be introduced to the vulnerable tissue site in one of several ways, including: (1) surgical methods, such as cut-down or laparoscopically; (2) intra-endoscopically, i.e., through the same body conduit or lumen as the one including the vulnerable tissue; and (3) inter-endoscopically, i.e., through, at least in part, a body conduit or lumen adjacent the conduit which has the vulnerable tissue.

By way of example, and not as a limitation, in describing the method of the present invention, only a subset of the various embodiments of the containment members of the present invention may be used. It should be appreciated by those skilled in the art that the more conventional steps of the method may not be individually described hereinafter.

Figure 23:
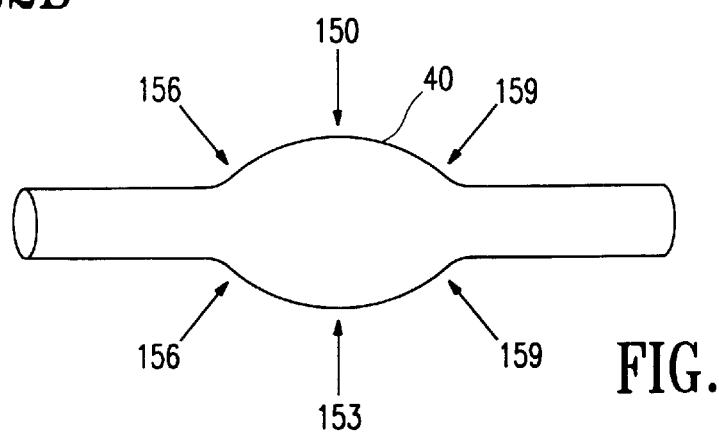
FIG. 23 is a side elevational view of a vulnerable tissue site showing the various access locations.

Now referring to FIG. 23 in a surgical method (cut-down or laparoscopically), an access site for accessing the vulnerable tissue site may be above or below the vulnerable tissue site 40, as for example, directly above or below, or proximal or distal to the site, as indicated by 150, 153, 156 and 159, respectively.

FIGS. 24–29 schematically depict a procedure whereby a containment member 10R, under imaging guidance; such as fluoroscopic techniques, ultrasound (e.g. catheter-based on external), angioscope, direct visualization, MRI, (including catheter-based and external), and CT scan; is disposed about the exterior surface of an vulnerable tissue site 40D of a patient included in a first body lumen 167. The containment member 10R is introduced over the surface of the aneurysm by percutaneous means through a lumen 170 of a catheter 173 through an access site 176, the containment member 10R and the catheter 173 together forming a delivery system 180. The catheter may be in the form of a hypotube or tubular member. A distal end of the catheter may include a curve, or may form a curve on demand. The catheter can be formed of any conventional material for forming such devices. The distal end 183 of catheter 173 is advanced to a location, distal or proximal, to the aneurysm 10R. Using a suitable mechanism such as a pusher rod, the containment member 10R is then advanced within the inner lumen 170 of the catheter 173, preferably, the catheter having a detachment mechanism 186 disposed at the catheter distal end 183

Figure 28:
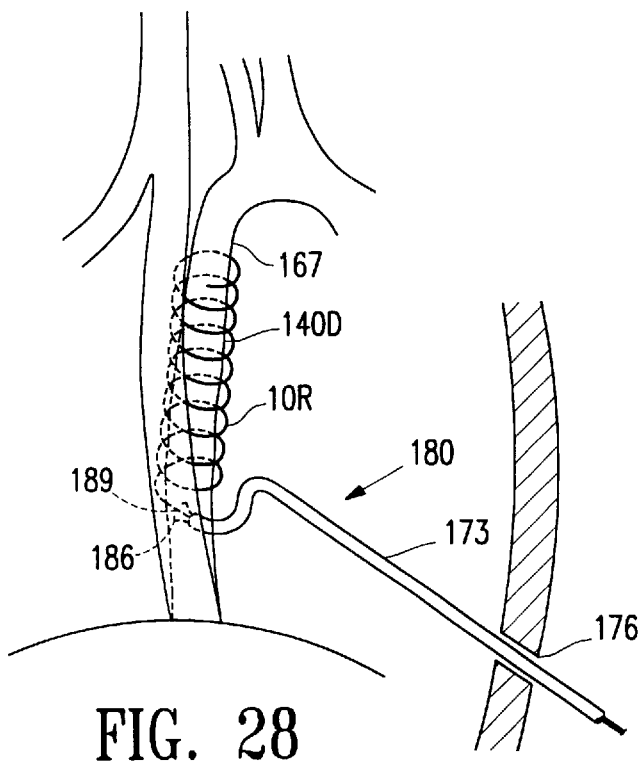
Figure 29:
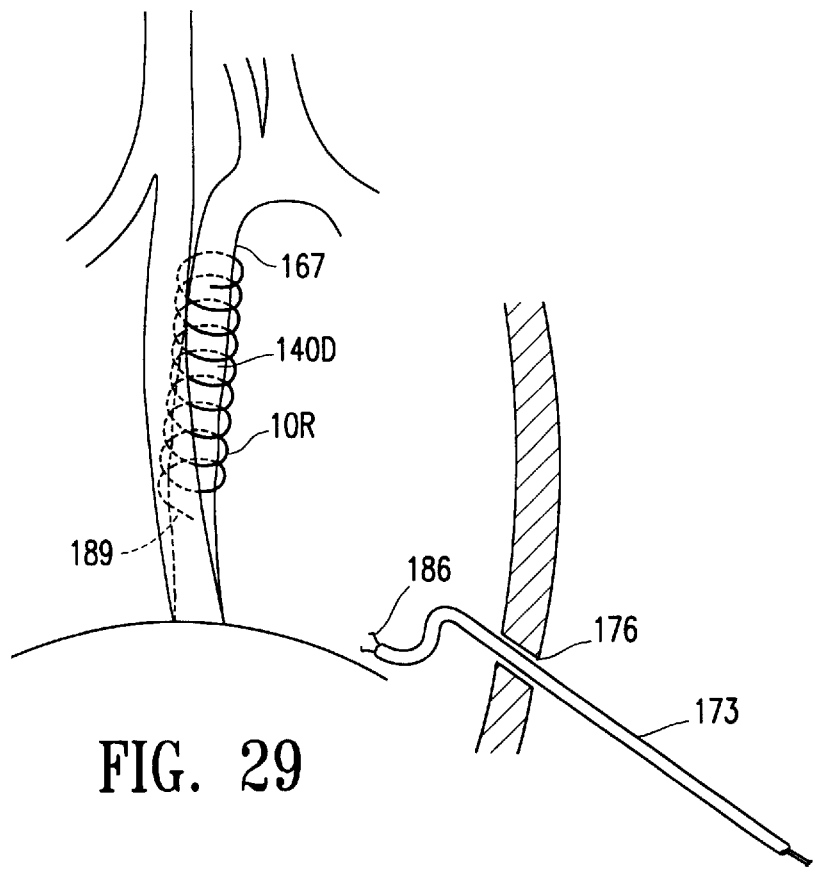
Figure 30:
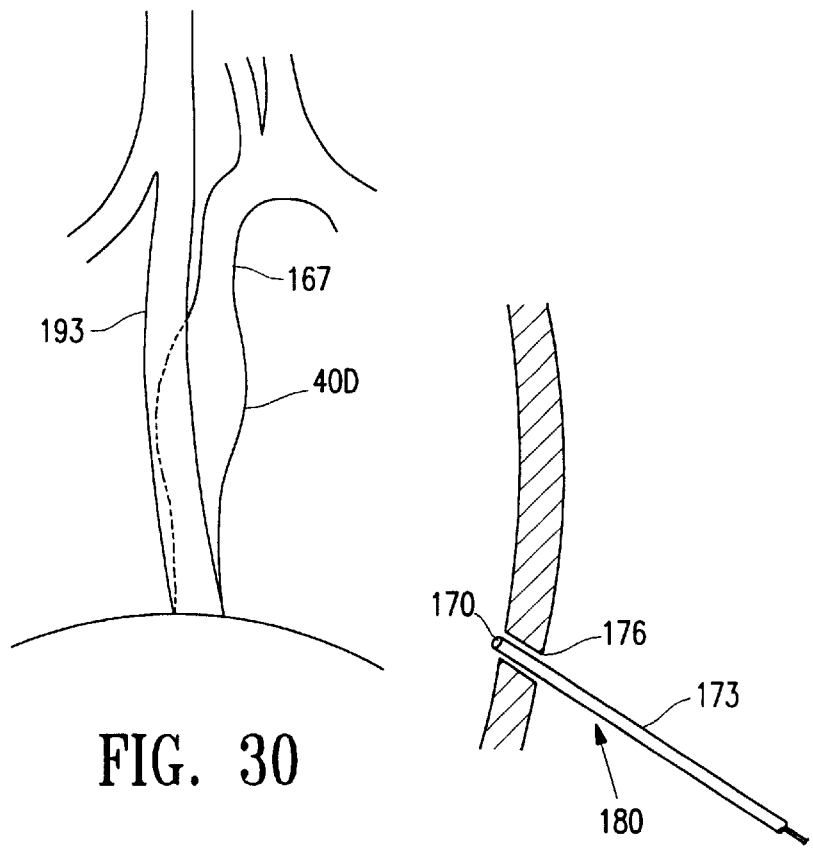
FIGS. 30–35 are schematic side elevational views of the steps of another surgical method disposing a containment member about the exterior surface of the first body lumen including the vulnerable tissue site and a second body lumen substantially parallel and adjacent the first body lumen.
Figure 31:
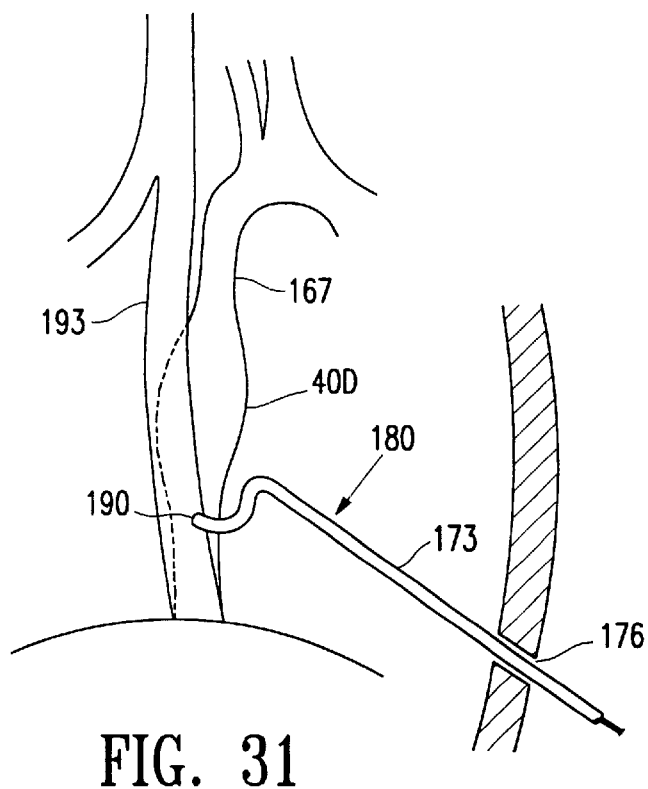
Figure 32:
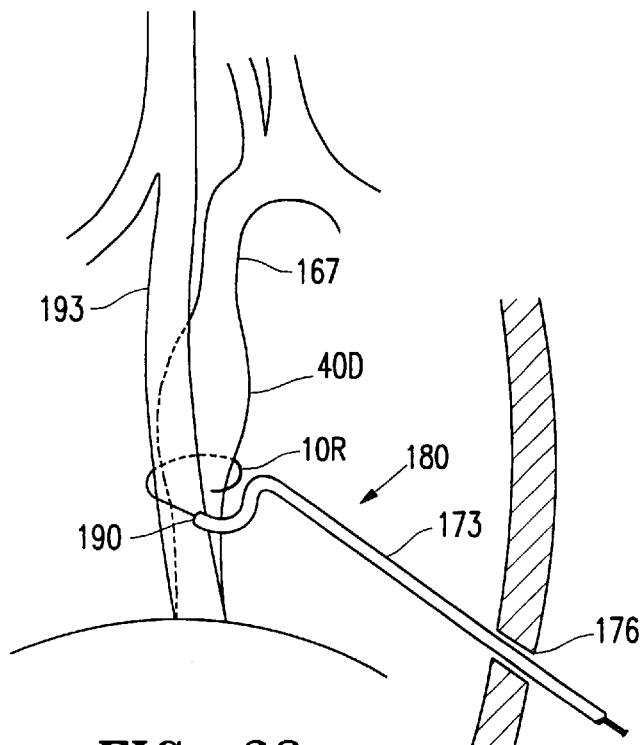
Figure 33:
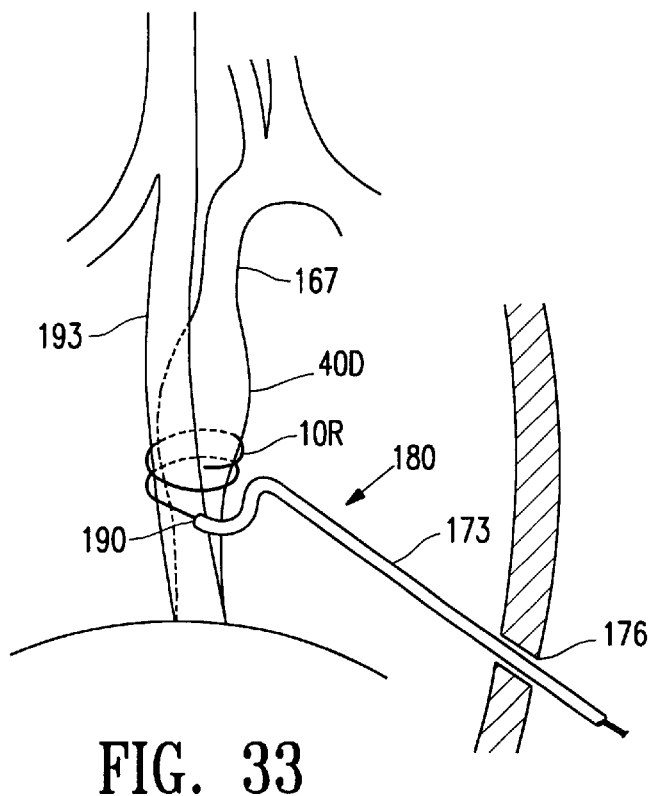
Figure 34:
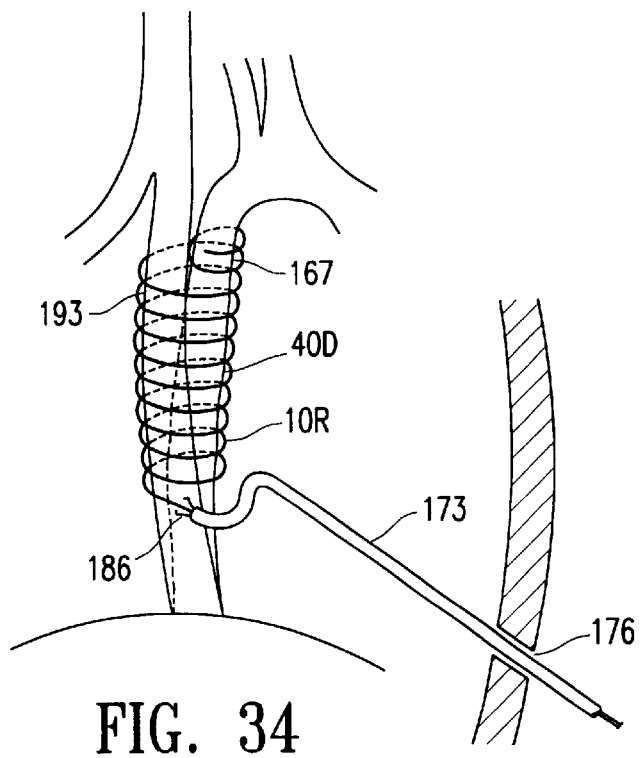
Figure 35:
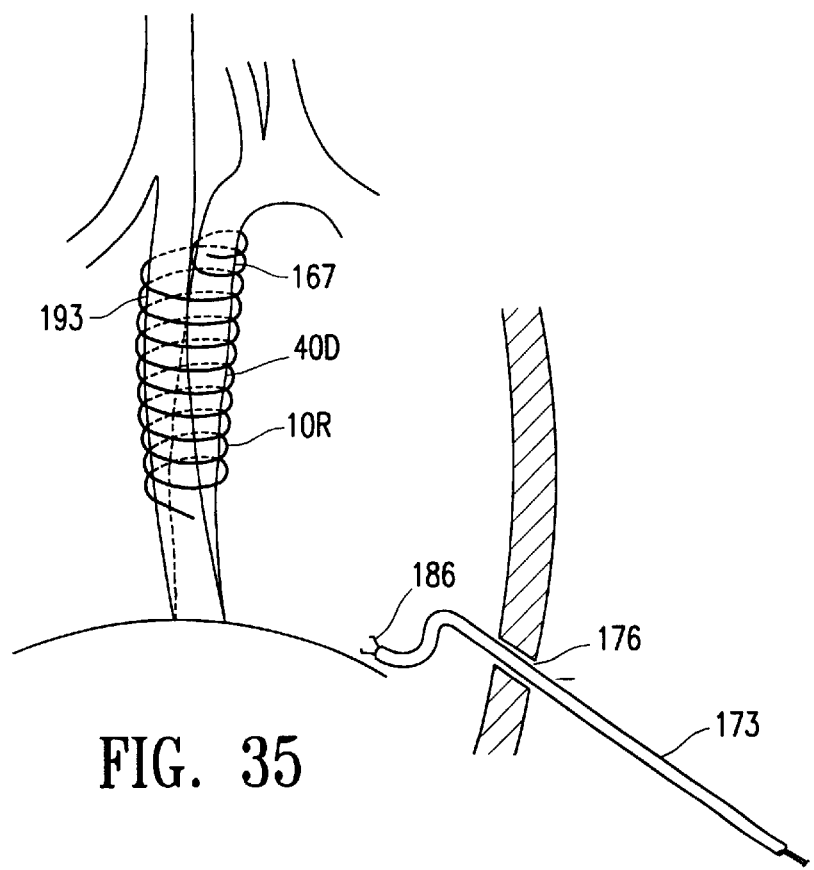
Figure 36:
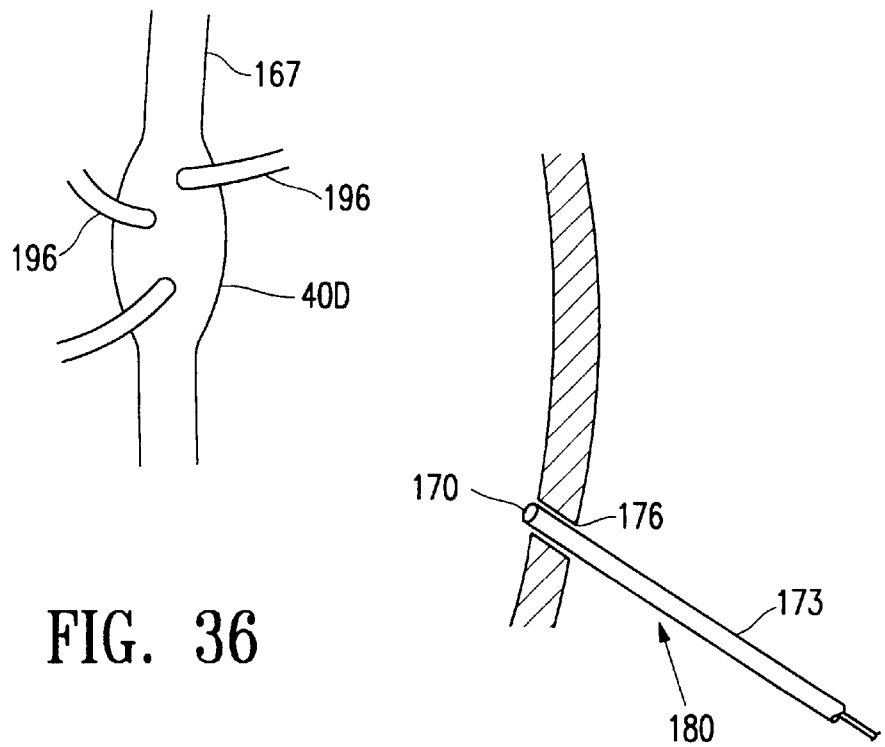
FIGS. 36–43 are schematic side elevational views of the steps of another surgical method disposing a containment member about the exterior surface of the first body lumen which includes peripheral branches.
Figure 37:
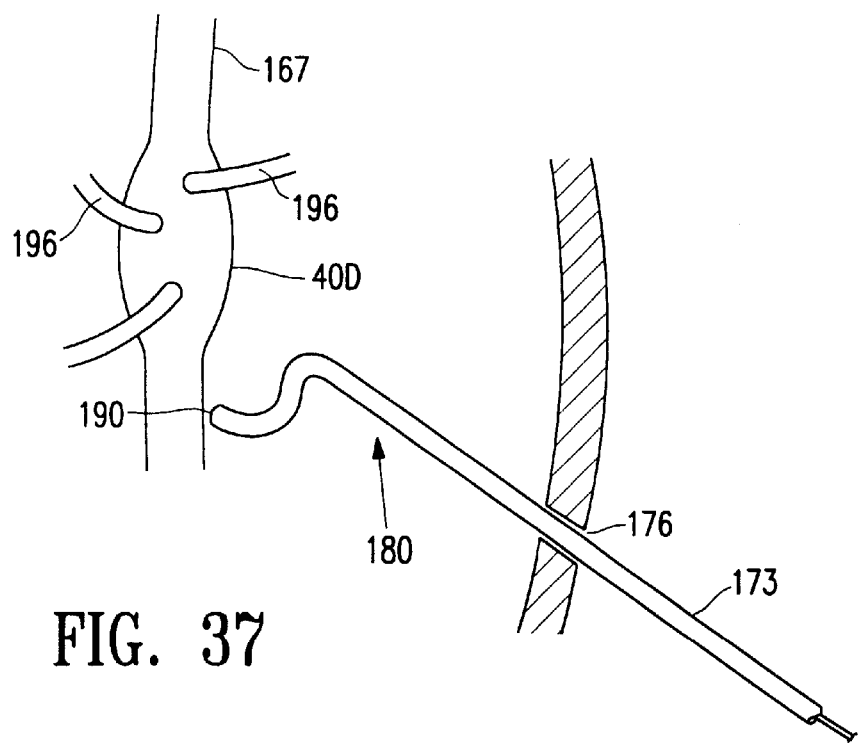
Figure 38:
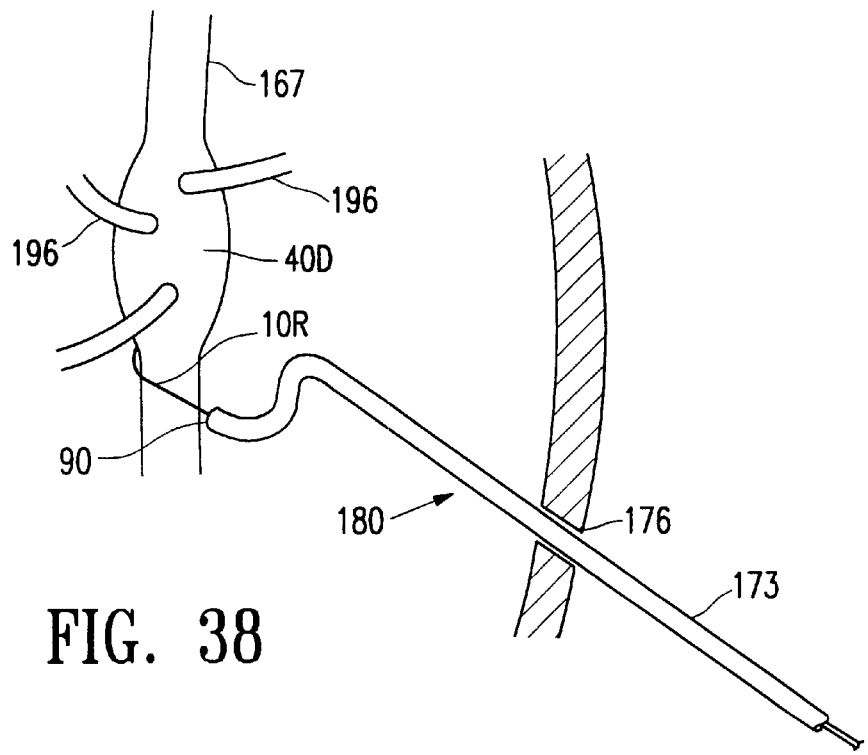
Figure 39:
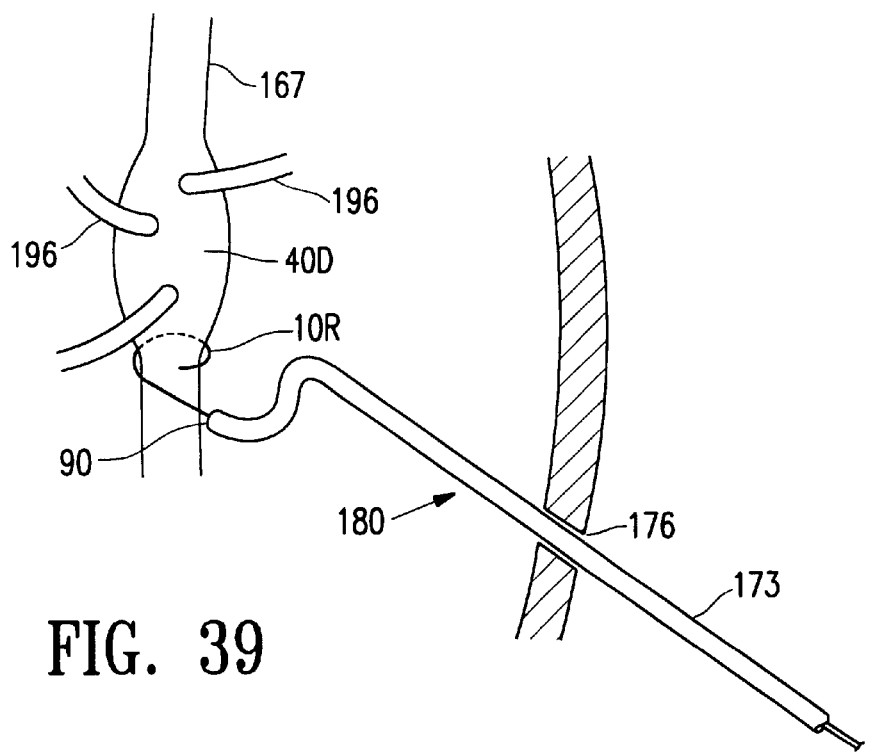
Figure 40:
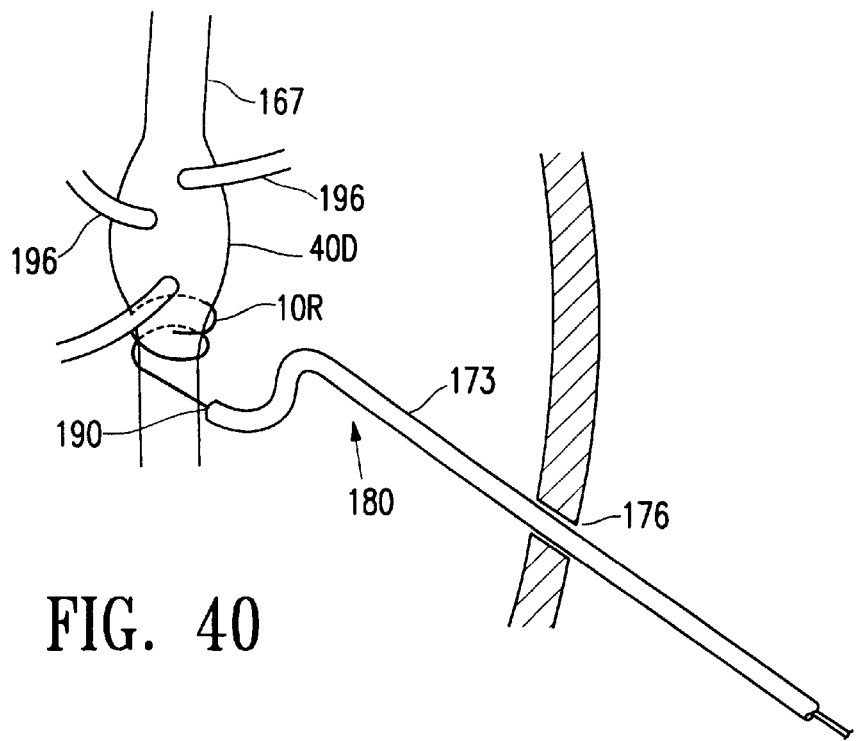
Figure 41:
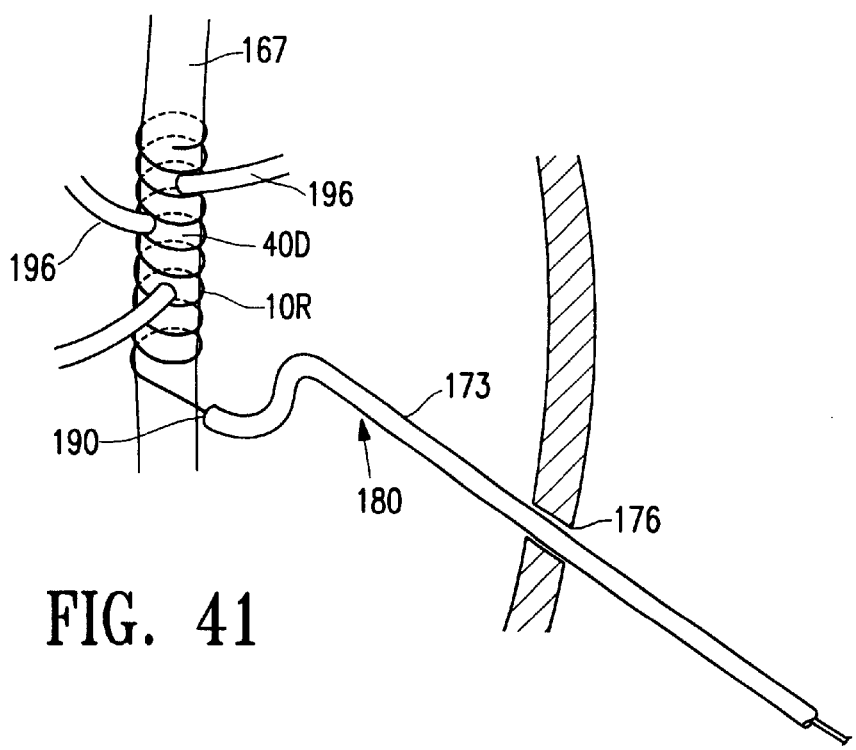
Figure 42:
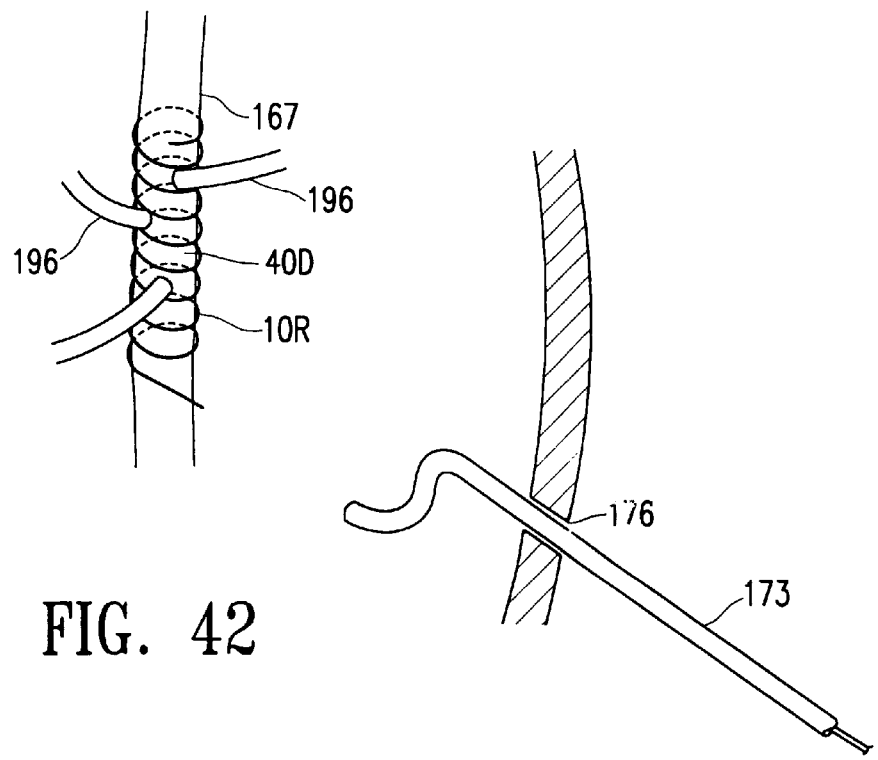
Figure 43:
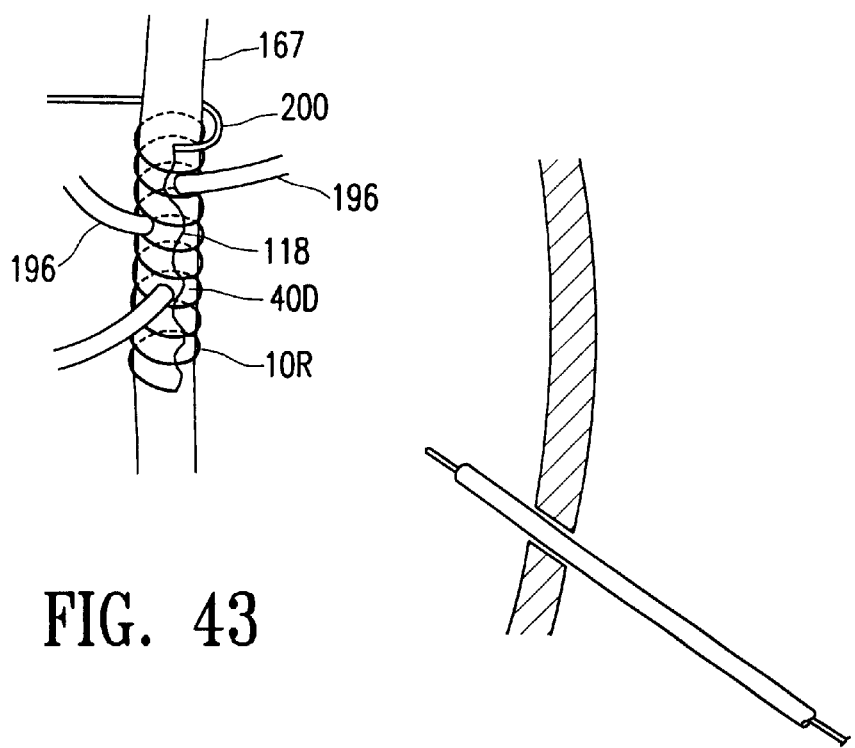
Figure 44:
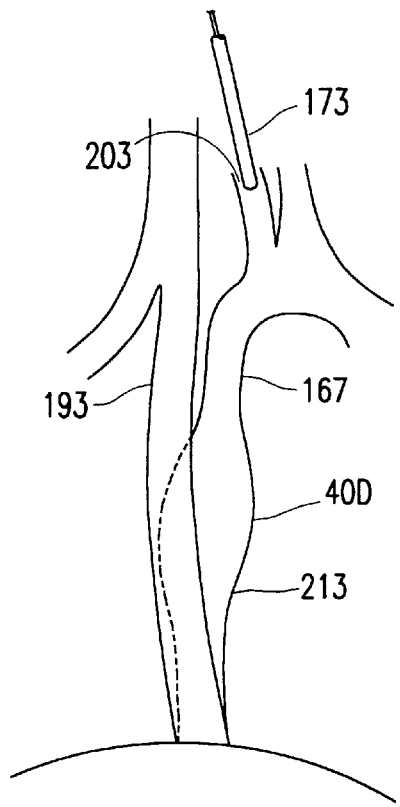
FIGS. 44–47 are schematic side elevational views of the steps of an intra-endoscopic method introducing a containment member through an inner lumen of the first body lumen and being disposed about the exterior surface of the first body lumen.
Figure 45:
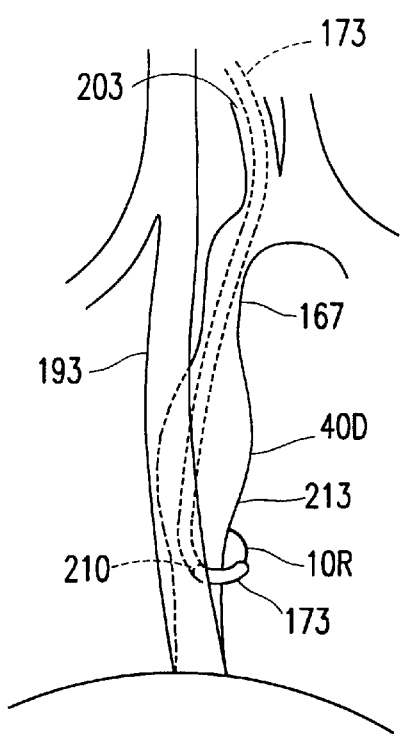
Figure 46:
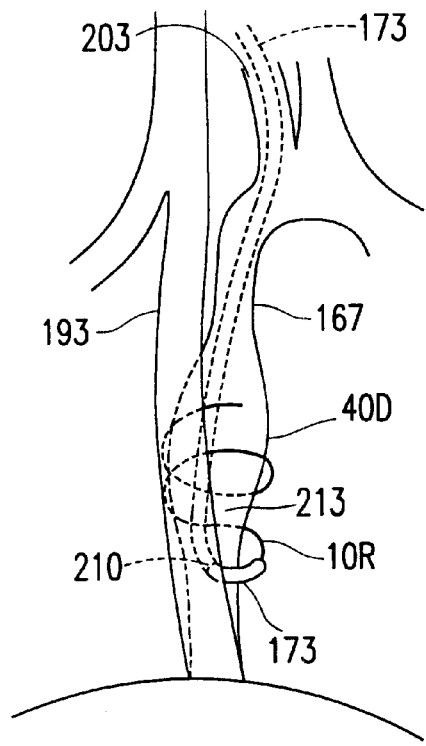
Figure 47:
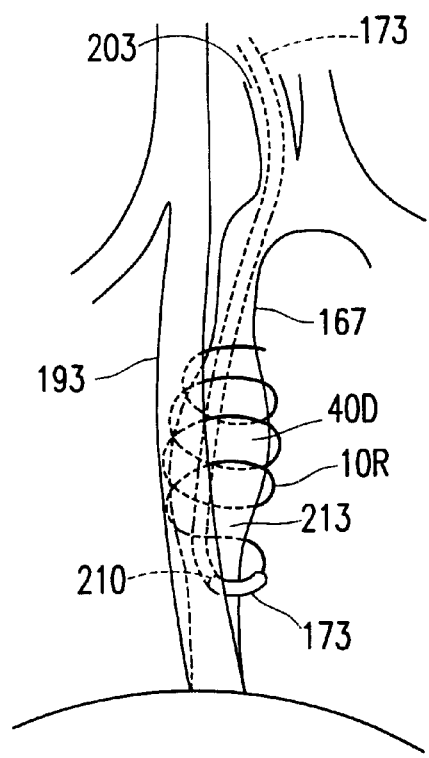
Figure 50:
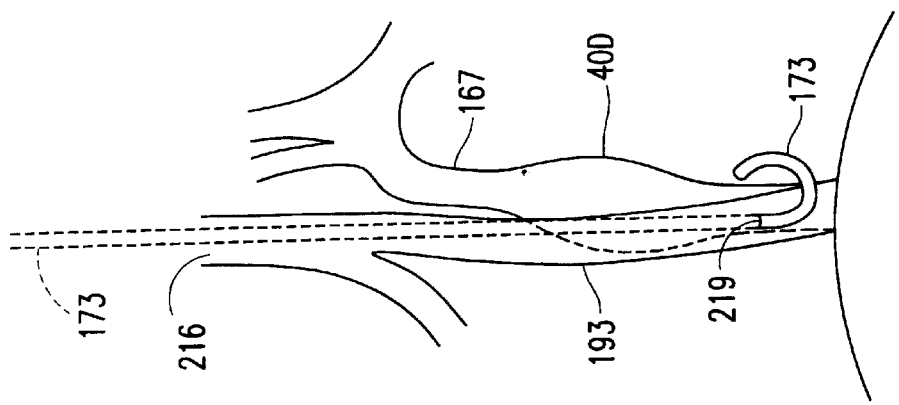
FIGS. 48–53 are schematic side elevational views of the steps of an inter-endoscopic method introducing a containment member through an inner lumen of the second body lumen and being disposed about the exterior surface of the first body lumen.
Figure 49:
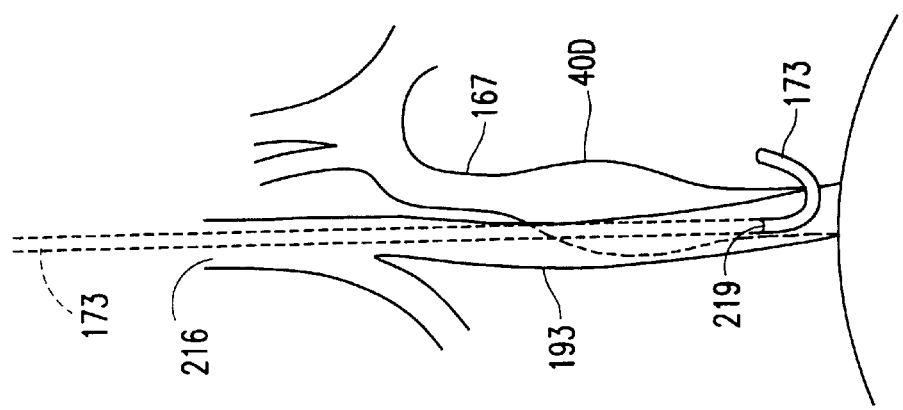
Figure 48:
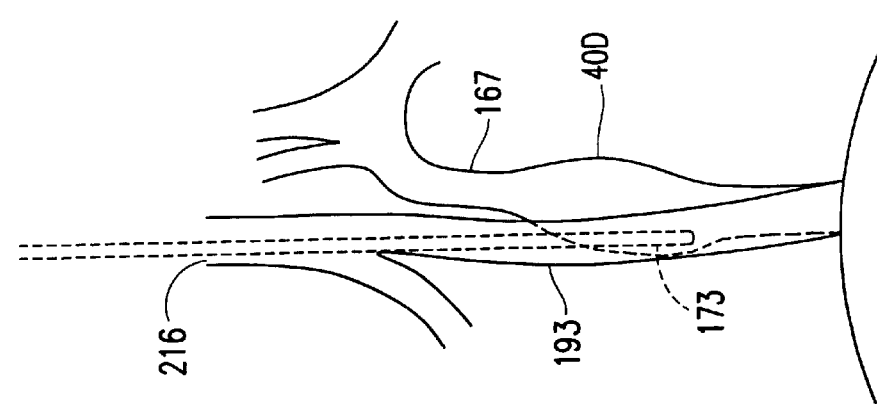
Figure 53:
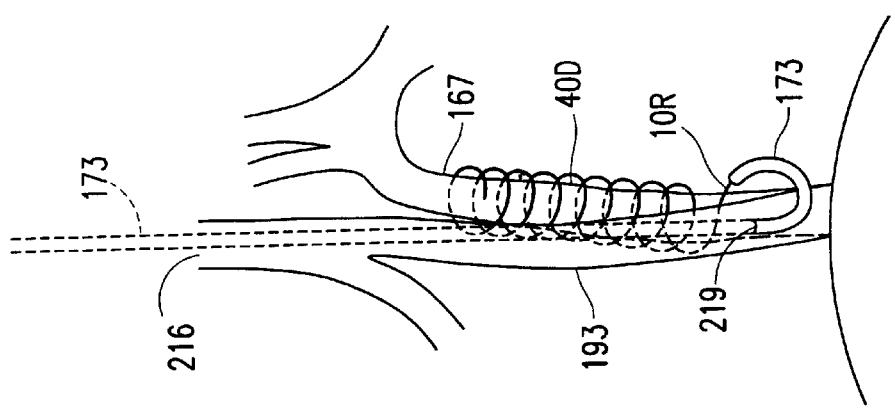
Figure 52:
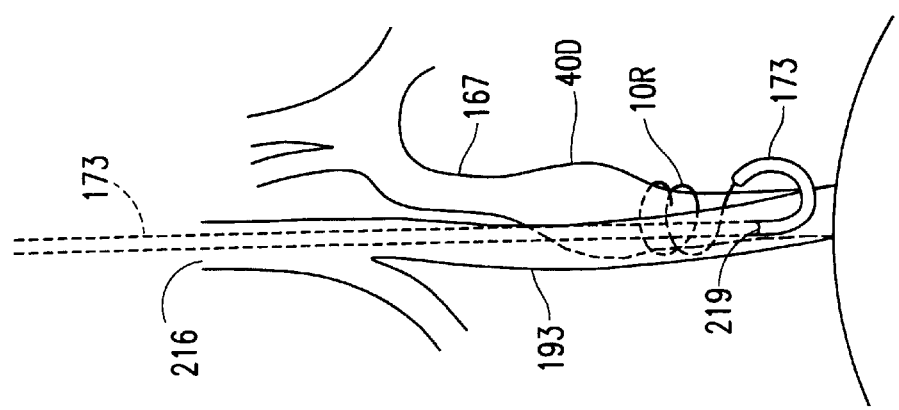
Figure 51:
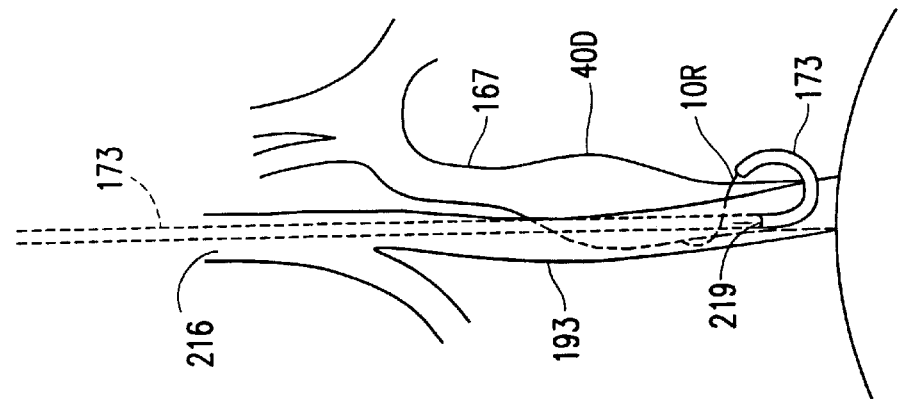
Figure 56:
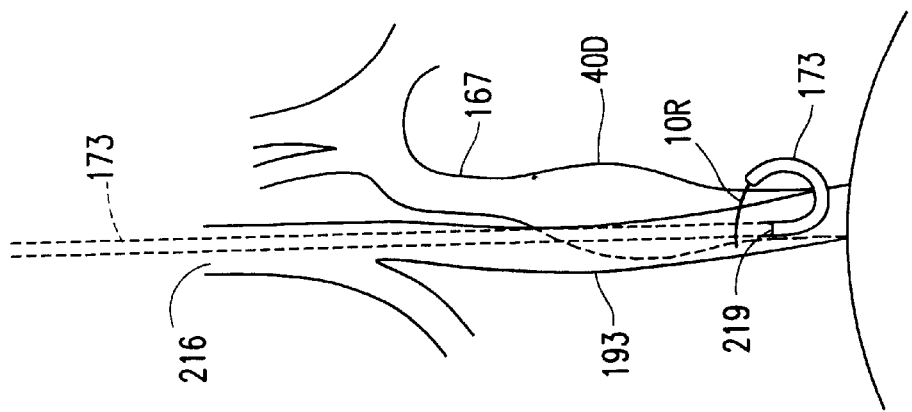
FIGS. 54–59 are schematic side elevational views of the steps of another intra-endoscopic method introducing a containment member through an inner lumen of the first body lumen and being disposed about the exterior surface of the first and second body lumens.
Figure 55:
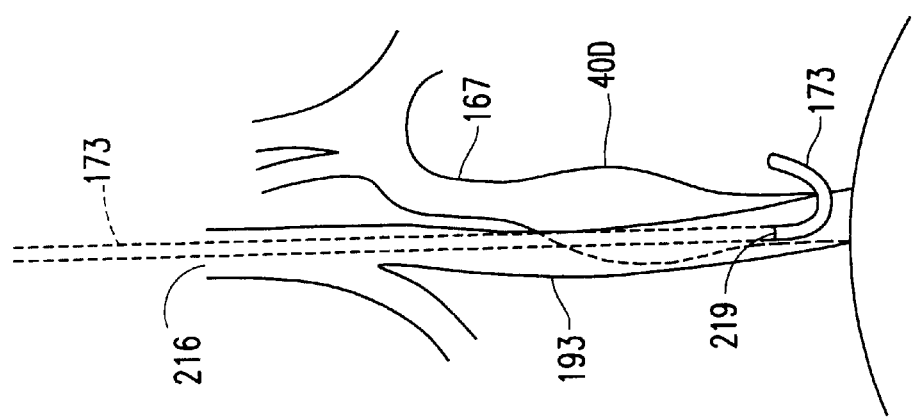
Figure 54:
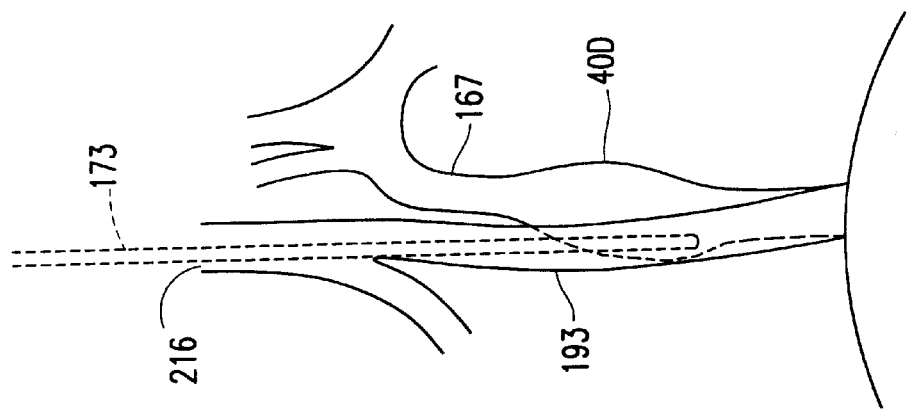
Figure 59:
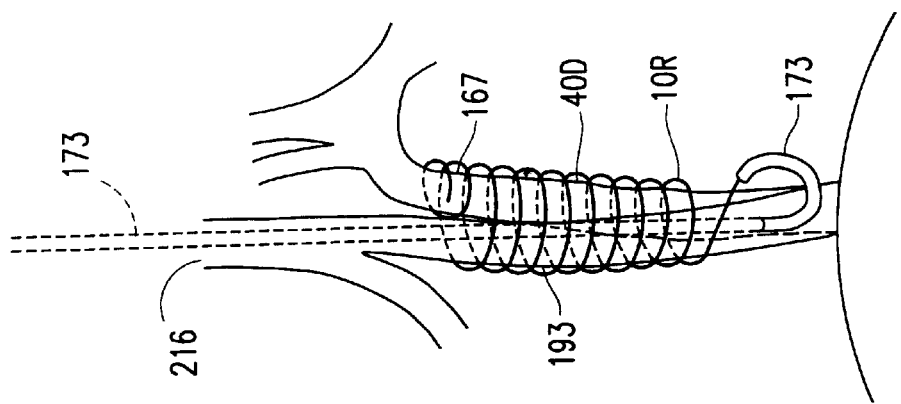
Figure 58:
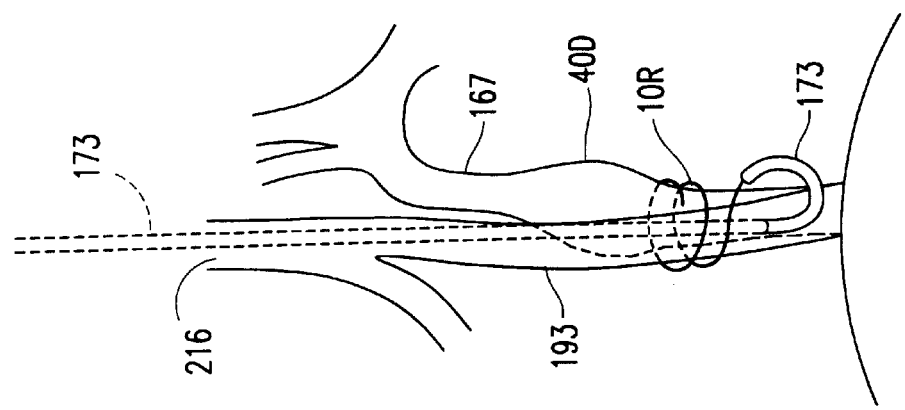
Figure 57:
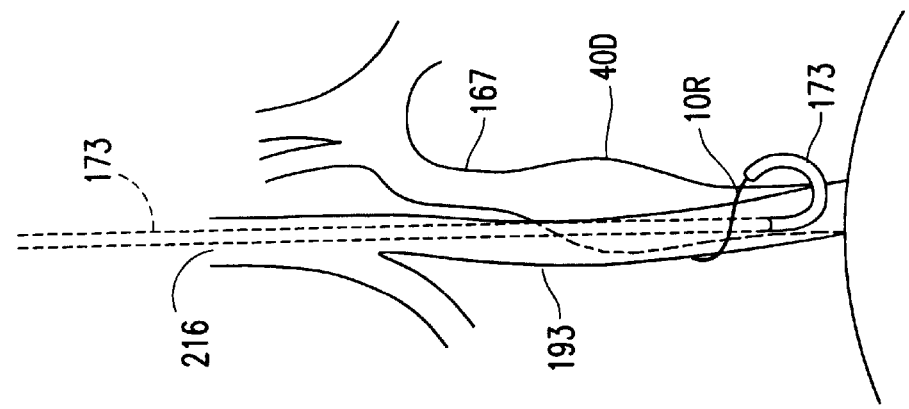

(FIG. 28). The detachment mechanism 186 is detachably secured to a proximal end 189 of the containment member 10R which allows proximal manipulation of the delivery system 180 to control axial advancement and retraction containment member 10R within the catheter 173 and the patient. The containment member 10R is then distally advanced out of a port 190 in the distal end 183 of the catheter 173 along the exterior surface of a body site which includes the vulnerable tissue 40, so as to contain at least a portion of the length of the vulnerable tissue 40. When the containment member 10R is appropriately positioned, the containment member 10R is detached from the delivery system 180 and is left in place and the catheter 173 is withdrawn from the body. The catheter 173 catheter can have multiple lumens (e.g. separate lumens for receiving the guidewire, containment member, light or visualization means, and drug delivery lumen). The catheter can also be inserted through a guiding catheter or sleeve having a pre-set shape at it is distal end according to the anatomy to be treated. Furthermore, the catheter can be a fixed wire type, over the wire type, or rapid exchange type.

It should be appreciated that the containment member 10R may be advanced onto the exterior surface of the aneurysm in an ascending direction, as shown in the figures, or in a descending direction, depending on the location of the introduction of the catheter; from above or below the site.

Examples of suitable detachment mechanisms include polymeric links susceptible to chain cleavage upon degradation of the polymer link, mechanical detachment, electrolytic detachment, shape memory metal or polymer activation via a temperature change by application of RF energy, laser energy, ultrasonic energy, heating of a hot melt adhesive joint, ultrasonic joint degradation, hydrokinetic activation of a mechanical retaining device, and the like. Various detachment mechanisms known in the art are discussed in U.S. Pat. Nos. 5,722,989, J. Fitch et al., U.S. Pat. No. 5,108,407, G. Geremia et al., U.S. Pat. No. 5,217,484, M. Marks, and U.S. Pat. No. 5,423,829, P. Pham, which are hereby incorporated by reference.

Alternatively, and as shown in FIGS. 30–35, the containment member 10R may be disposed about both the first body lumen 168 including the vulnerable tissue 40D and a second body lumen 193 substantially parallel to or adjacent the first body lumen. In FIGS. 30–35, the containment member 10R is laparoscopically introduced through the access site 176 and is advanced and disposed about, at least in part, both the esophagus as the second body lumen and the vulnerable tissue site 40D (e.g. aneurysm) located in the aorta as the first body lumen.

Often, the vulnerable tissue 40D, may be located in a part of the body which includes peripheral branches, as for example, peripheral branches of aorta. FIGS. 36–43 show the steps associated with disposing the containment member 10R about the exterior surface of the first body lumen 167 which includes peripheral branches 196. In the practice of this method, it is particularly useful, to use a helical containment member 10A similar to that previously shown in FIG. 2 (or one or more omega shaped containment members such as that shown in FIG. 8). The helical configuration of the containment member allows the advancement of the containment member along the exterior surface of the length of the first body lumen without being impeded by the peripheral branches. As shown in the figures, the containment member may optionally be secured in place by the use of a suitable device 200 to tie or tighten the coils with suture 118 or other means. Alternatively, when the containment member is formed from a shape-memory material, such as Nitinol, the containment member may be secured in place by the application of heat or energy, thus, transforming its size and dimensions. The containment member can be pre-shaped to the desired configuration (in the disposed configuration) and constrained to a secondary shape by the catheter such that upon release (e.g., disposing about the vulnerable tissue site) the containment member assumes the desired disposed shape.

Now referring to FIGS. 44–47 in a intra-endoscopic method, the catheter 173 is introduced through an inner lumen 203 of a first body lumen 167 which includes the vulnerable tissue 40D, from a location proximal or distal (above or below) to the vulnerable tissue. Similar to the surgical method, the catheter 173 is advanced along the interior lumen 203 of the first body lumen 167 to an access point 210 being proximal or distal to the vulnerable tissue 40D, at which point the catheter 173 is advanced through wall 213 of the first body lumen 167 and unto the exterior surface of the first body lumen (or body site). The containment member is then advanced onto the vulnerable tissue similar to the surgical method described above.

Now referring to FIGS. 48–53 in a inter-endoscopic method, the catheter 173 is introduced through an inner lumen 370 of the second body lumen 193 extending either or both substantially parallel, at least in part, and adjacent, at least in part, to the first body lumen 137 which includes the vulnerable tissue 4D. The catheter 173 is then advanced through access site 219 located in a wall of the second body lumen and unto the exterior surface of the first body lumen (or body site). The containment member 10R is then advanced onto the vulnerable tissue similar to the surgical method described above.

The inter-endoscopic method is particularly useful when a relatively easily accessible second body lumen lies substantially parallel or adjacent to the first body lumen having the vulnerable tissue. For example when the aneurysm is located is in the thoracic cavity, the esophagus can be a suitable second lumen for accessing the aneurysm located in the thoracic aorta.

Alternatively, and as depicted in FIGS. 54–59, in the operation of the inter-endoscopic method, the containment member 10R may be disposed, at least in part, along the exterior surface of both the first and the second body lumens, 167 and 193, once it exits the wall of the second body lumen.

Figure 62:
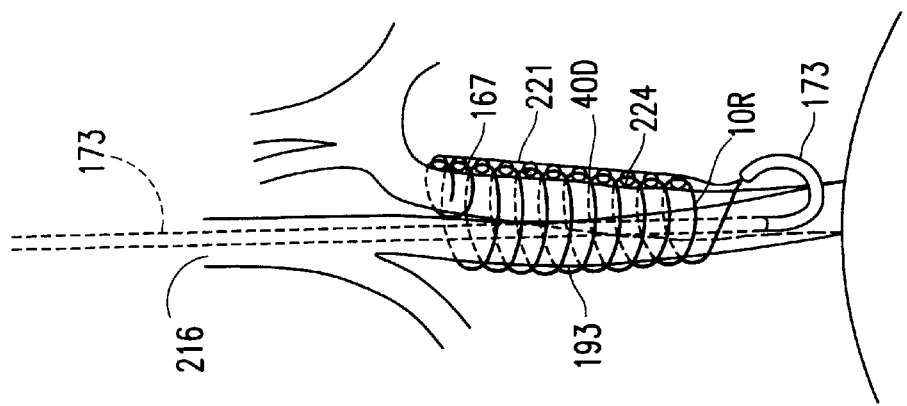
FIGS. 60–62 are schematic side elevational views of the steps of another intra-endoscopic method introducing a containment member through an inner lumen of the first body lumen and being disposed about the exterior surface of the first and second body lumens and further including an elongate glide for securing the containment member to the tissue site.
Figure 61:
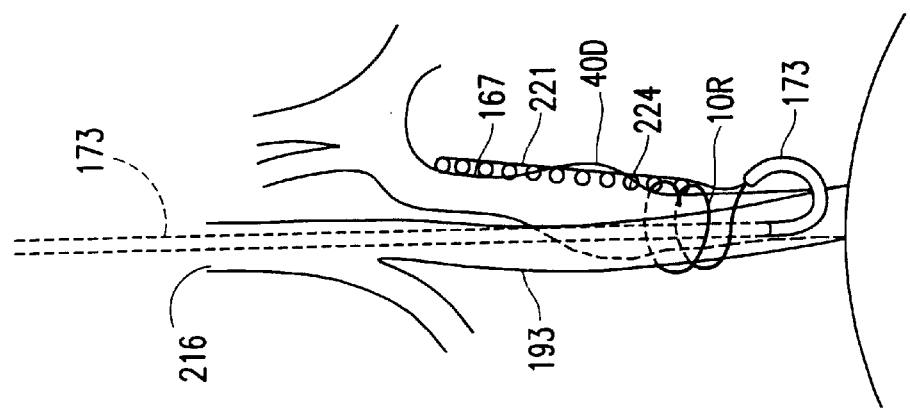
Figure 60:
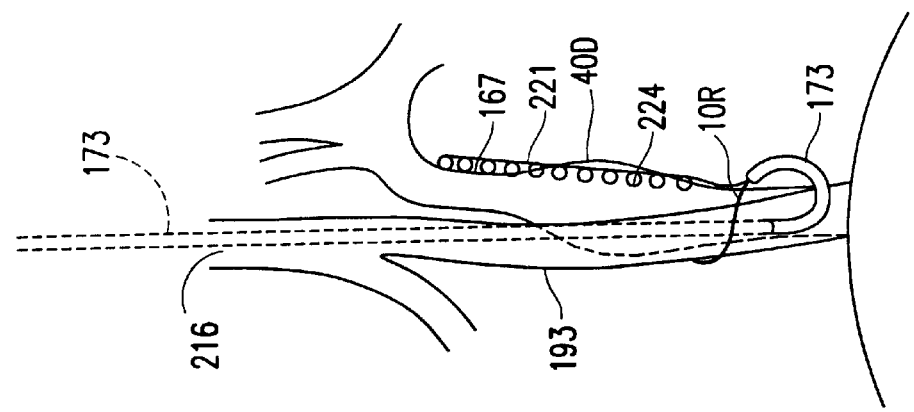

In yet another embodiment, shown in FIGS. 60–62, the catheter 173 may be equipped to deliver an elongate glide 221 used to secure the containment member 10R along the exterior surface of the first body lumen 167. The glide 221, includes loops 224 along its length. Once advanced out of the catheter 173, the glide 2210 is secured to the first body lumen at various points along its length. The containment member 10R as it is being advanced along the exterior surface of the length of the vulnerable tissue, is looped through the glide loops 224, thus, becoming secure in place. For example, sutures can be passed through one or more of the glide loops to secure the glide to the first body lumen. Alternatively, the containment member 10R may be secured to the exterior surface of the vulnerable tissue site by other suitable means, such as adhesives.

Now referring to FIGS. 63–65, when the vulnerable tissue 40 is on a body site such as an organ, containment member 10S can be advanced by way of any one of the methods described above and disposed on the exterior surface of the organ. In operation, one or more individual containment members may be disposed on the organ in the same or differing orientations, as shown in the FIGS. 63–65. The containment member may only act to contain the vulnerable tissue site minimizing its further growth or it may apply pressure or compressive force on the vulnerable tissue site 40 tissue thereby reducing its size, as depicted in FIGS. 63, 64A and 64B; and or 65A, 65B, and 65C.

Figure 66A:
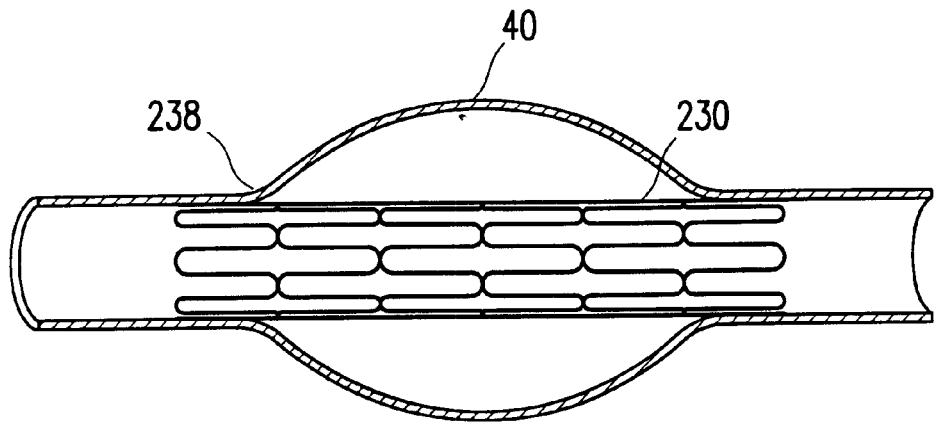
FIGS. 66A–66C are side elevational views of the containment members embodying features of the present invention used in combination with a stent graft.
Figure 66B:
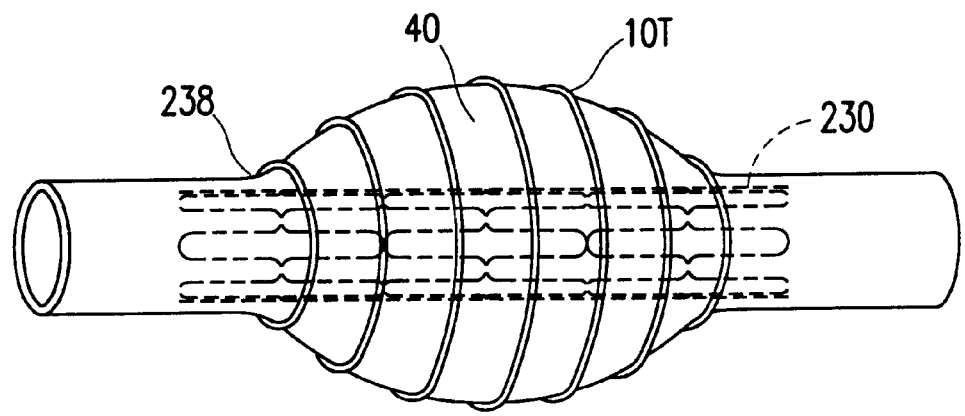
Figure 66C:
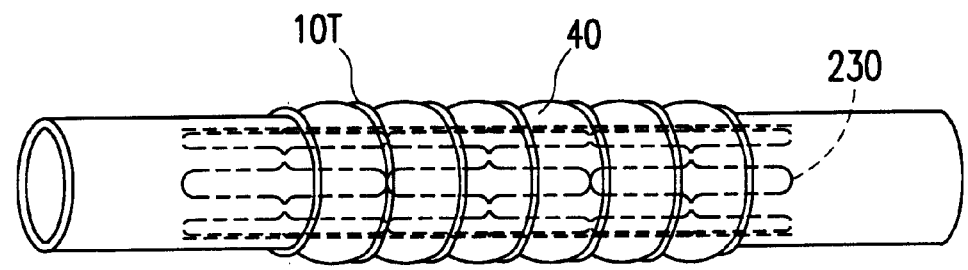
Figure 67A:
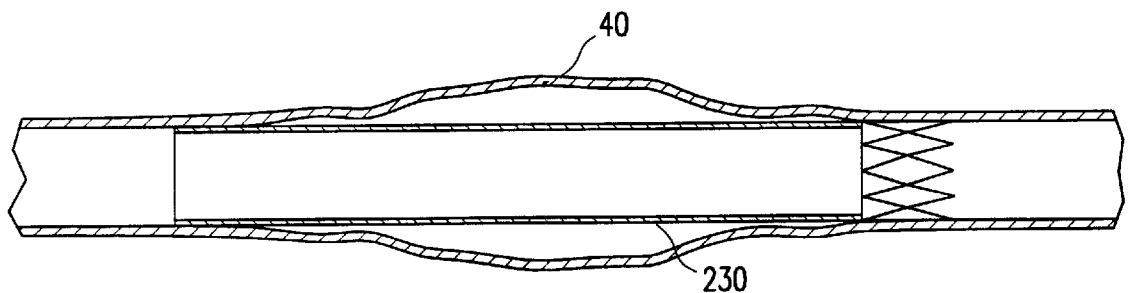
FIGS. 67A–67C are side elevational views of the containment members embodying features of the present invention used in combination with a stent graft with the two ends of the containment member defining a neck and extending onto the adjacent healthy tissue site.
Figure 67B:
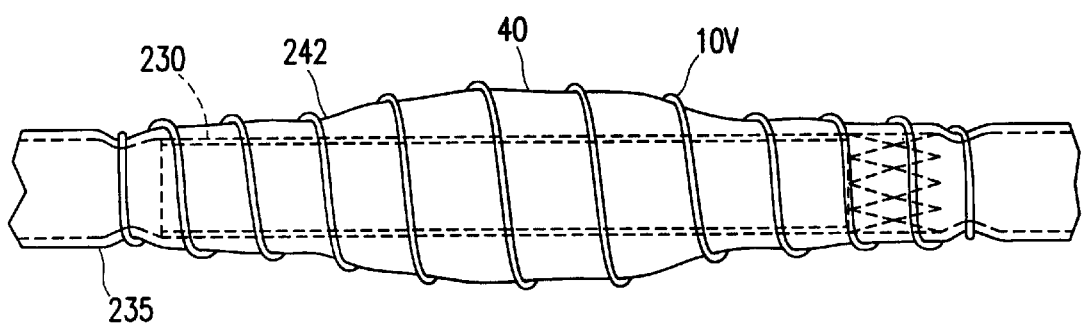
Figure 67C:
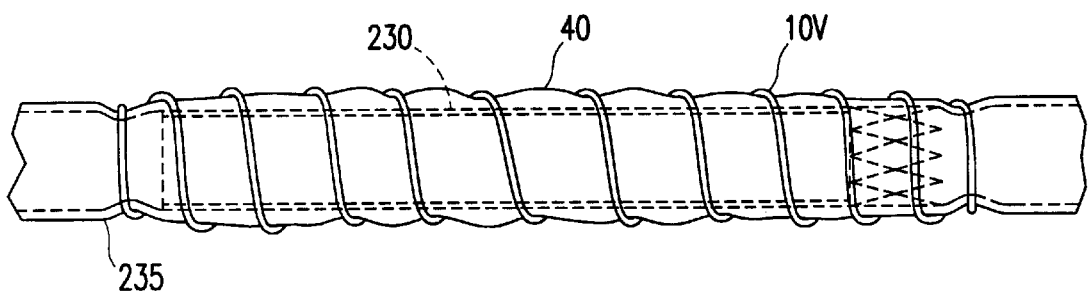

As shown in FIGS. 66 through 67, the containment members of the present invention can be used in conjunction with a stent/graft 230. In the embodiment shown in FIGS. 66B and 66C, the containment member 10T is shown enclosing longitudinally, at least in part, the vulnerable tissue 40. The containment member may only contain the vulnerable tissue site or it may act to reduce its size, immediately or over time, as shown in FIG. 66C. Alternatively, as shown in FIG. 67A, there may not be a well defined neck (such as 238 in FIG. 66A) on either or both sides of the vulnerable tissue site for having the stent/graft abutting against. In this configuration, as shown in FIGS. 67B and 67C, either or both the proximal and distal ends of the containment member 10V can extend to cover healthy tissue 235 (i.e., not-vulnerable tissue) on either or both sides of the vulnerable tissue 40 or compress vulnerable tissue to define a neck, whereby, the compression of the containment member 10V onto the vulnerable tissue site aids in creation of a neck 242 thereby aiding in the securing of the of the stent/graft 230 within the body lumen of the aneurysm. It should be noted that the containment members, may contain the vulnerable tissue site 40 with or without application of pressure to the site.

While particular forms of the invention have been illustrated and described, it will be apparent that various modifications can be made without departing from the spirit and scope of the invention. Accordingly, it is not intended that the invention be limited.

What is claimed is:

1. A method for treating a patient's aortic aneurysm which has an expanded weakened aortic wall extending over a length of the patient's aorta, comprising, providing a tubular containment member; and advancing the tubular containment member through a lumen of the aorta and through an access site in a wall of the aorta and disposing the containment member about an exterior surface over at least a length of the weakened aortic wall of the aortic aneurysm to support the weakened aortic wall.

2. A method for treating a patient's aortic aneurysm which has an expanded weakened aortic wall extending over a length of the patient's aorta, comprising, providing a tubular containment member; and advancing the tubular containment member through a lumen of a second tubular body member disposed, at least in part, substantially parallel and adjacent the weakened aortic wall of the aortic aneurysm and through an access site in the second tubular body member and disposing the containment member about an exterior surface over at least the length of the weakened aortic wall of the aortic aneurysm to support the weakened aortic wall to resist further expansion thereof.

3. The method of claim 2 wherein the access site is located in a wall of the second tubular body.

4. The method of claim 2 wherein the second tubular body includes any one of esophagus, trachea, or vena cava.

* * * * *